US012599293B2

(12) United States Patent
Tanigami et al.

(10) Patent No.: US 12,599,293 B2
(45) Date of Patent: Apr. 14, 2026

(54) ASSIST DEVICE, ENDOSCOPE SYSTEM, ASSIST METHOD AND COMPUTER-READABLE RECORDING MEDIUM

(71) Applicant: OLYMPUS CORPORATION, Tokyo (JP)

(72) Inventors: Yasuo Tanigami, Tokyo (JP); Yusuke Otsuka, Yokohama (JP); Noriko Kuroda, Machida (JP); Takaaki Igarashi, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 509 days.

(21) Appl. No.: 18/119,512

(22) Filed: Mar. 9, 2023

(65) Prior Publication Data

US 2023/0210354 A1 Jul. 6, 2023

Related U.S. Application Data

(63) Continuation of application No. PCT/JP2020/036945, filed on Sep. 29, 2020.

(51) Int. Cl.
 *A61B 1/04* (2006.01)
 *A61B 1/00* (2006.01)
 *A61B 1/018* (2006.01)
(52) U.S. Cl.
 CPC ............ *A61B 1/043* (2013.01); *A61B 1/0005* (2013.01); *A61B 1/00186* (2013.01); *A61B 1/018* (2013.01)
(58) Field of Classification Search
 CPC ... A61B 1/00062; A61B 1/043; A61B 5/0071; A61B 5/4842; A61B 5/4848;
(Continued)

(56) References Cited

U.S. PATENT DOCUMENTS

2004/0236606 A1* 11/2004 Oishi ..................... A61B 90/98
 705/2
2008/0097174 A1* 4/2008 Maynard ............ G01N 21/6408
 600/316
(Continued)

FOREIGN PATENT DOCUMENTS

CN 104548383 A 4/2015
CN 105263576 A 1/2016
(Continued)

OTHER PUBLICATIONS

International Search Report dated Dec. 8, 2020 received in PCT/JP2020/036945.

(Continued)

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An assist device includes: a processor configured to generate a fluorescence image based on an imaging signal that is generated by capturing an image of fluorescence caused by excitation light that is applied to a living tissue, calculate a fluorescence intensity based on the fluorescence image, based on the fluorescence intensity, estimate a placement period during which a medical tool is placed in a lumen, and output placement period information on the placement period and an observation image obtained by capturing an image of the living tissue.

13 Claims, 15 Drawing Sheets

(58) Field of Classification Search

CPC .............. A61B 5/4851; A61B 5/7275; A61B 17/12118; A61B 18/12; A61B 2018/00005; A61B 2018/00267; G16H 20/40

See application file for complete search history.

(56) References Cited

U.S. PATENT DOCUMENTS

| | | | |
|---|---|---|---|
| 2011/0178411 A1* | 7/2011 | Roth | A61B 5/0036 424/9.2 |
| 2015/0045882 A1 | 2/2015 | Fox et al. | |
| 2015/0133728 A1 | 5/2015 | Finkman et al. | |
| 2015/0196202 A1* | 7/2015 | Mercader | A61B 1/043 600/478 |
| 2015/0305604 A1* | 10/2015 | Melsky | A61B 18/20 600/104 |
| 2016/0081701 A1 | 3/2016 | Honda | |
| 2016/0113573 A1 | 4/2016 | Arai et al. | |
| 2016/0135894 A1 | 5/2016 | Finkman et al. | |
| 2017/0084024 A1* | 3/2017 | Gurevich | G06T 7/0012 |
| 2017/0119559 A1 | 5/2017 | Seguy et al. | |
| 2017/0354357 A1* | 12/2017 | Laughner | A61B 5/6852 |
| 2018/0242848 A1* | 8/2018 | Dacosta | A61B 5/742 |
| 2019/0358387 A1* | 11/2019 | Elbadry | G01N 15/06 |
| 2020/0078602 A1* | 3/2020 | Hirsh | A61B 17/12186 |
| 2022/0343497 A1* | 10/2022 | Buurma | A61B 5/015 |
| 2023/0114323 A1* | 4/2023 | Bydlon | A61B 90/37 606/130 |
| 2024/0108392 A1* | 4/2024 | Sharma | A61B 5/01 |

FOREIGN PATENT DOCUMENTS

| | | |
|---|---|---|
| JP | 2014-128423 A | 7/2014 |
| JP | 2016-059709 A | 4/2016 |
| JP | 2016-540558 A | 12/2016 |
| JP | 2017-500172 A | 1/2017 |
| JP | 2017-510371 A | 4/2017 |
| JP | 2017-513645 A | 6/2017 |

OTHER PUBLICATIONS

Chinese Office Action dated May 28, 2025 received in 202080105586.1.

* cited by examiner

FIG.5

MAXIMUM DEGREE OF INVASION: XXX — m1

PLACEMENT OF STENT: NECESSARY — m2

PREFERRED PLACEMENT PERIOD: LONG — m3

P10

INVASION IS DETECTED

ASSIST DEVICE, ENDOSCOPE SYSTEM, ASSIST METHOD AND COMPUTER-READABLE RECORDING MEDIUM

CROSS-REFERENCE TO RELATED APPLICATION

This application is a continuation of International Application No. PCT/JP2020/036945, filed on Sep. 29, 2020, the entire contents of which are incorporated herein by reference.

BACKGROUND

1. Technical Field

The disclosure relates to an assist device for determining a placement period during which a stent is placed in a urinary tract, and an endoscope system, an assist method and a computer-readable recording medium.

2. Related Art

As for endoscopes, a technique of applying a laser beam to a calculus that is caused in a urinary tract to fragment the calculus has been known (refer to, for example, Japanese National Publication of International Patent Application No. 2017-500172). According to the technique, when it is confirmed that an aiming beam is incident on a target lump of calculus, or the like, an energy source is operated to apply an energy pulse onto the target lump via an energy guide. In this case, because there is a possibility that the ureter may be damaged, a stent is placed to protect the ureter after fragmentation of calculus (refer to, for example, Japanese National Publication of International Patent Application No. 2017-510371).

SUMMARY

In some embodiments, an assist device includes: a processor configured to generate a fluorescence image based on an imaging signal that is generated by capturing an image of fluorescence caused by excitation light that is applied to a living tissue, calculate a fluorescence intensity based on the fluorescence image, based on the fluorescence intensity, estimate a placement period during which a medical tool is placed in a lumen, and output placement period information on the placement period and an observation image obtained by capturing an image of the living tissue.

In some embodiments, an endoscope system includes: an endoscope that is insertable into a lumen of a subject; a light source configured to emit excitation light that excites advanced glycation end products caused by performing thermal treatment on a living tissue; and a control device that is detachable from the endoscope, the endoscope including an imaging device configured to generate an imaging signal by capturing an image of fluorescence caused by the excitation light, and a cut filter that is provided on a side of a light receiving surface of the imaging device, the cut filter being configured to block light on a side of short wavelengths containing part of a wavelength band of the excitation light, the control device including an assist device that assists a practitioner, and the assist devise including a processor configured to generate a fluorescence image based on the imaging signal, calculate a fluorescence intensity based on the fluorescence image, based on the fluorescence intensity, estimate a placement period during which a medical tool is placed in the lumen, and output placement period information on the placement period and an observation image obtained by capturing an image of the living tissue.

In some embodiments, provided is an assist method executed by an assist device. The method includes: generating a fluorescence image based on an imaging signal that is generated by capturing an image of fluorescence caused by excitation light that is applied to a living tissue; calculating a fluorescence intensity based on the fluorescence image; based on the fluorescence intensity, estimating a placement period during which a medical tool is placed in a lumen; and outputting placement period information on the placement period and an observation image obtained by capturing an image of the living tissue.

In some embodiments, provided is a non-transitory computer-readable recording medium with an executable program stored thereon. The program causes an assist device to execute generating a fluorescence image based on an imaging signal that is generated by capturing an image of fluorescence caused by excitation light that is applied to a living tissue; calculating a fluorescence intensity based on the fluorescence image; based on the fluorescence intensity, estimating a placement period during which a medical tool is placed in a lumen; and outputting placement period information on the placement period and an observation image obtained by capturing an image of the living tissue.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 5 is a diagram illustrating an example of correlation information that a correlation information recorder records according to the embodiment;

FIG. 17 is a diagram schematically illustrating transmission characteristics of a cut filter according to a modification of the embodiment.

DETAILED DESCRIPTION

Figure 1:
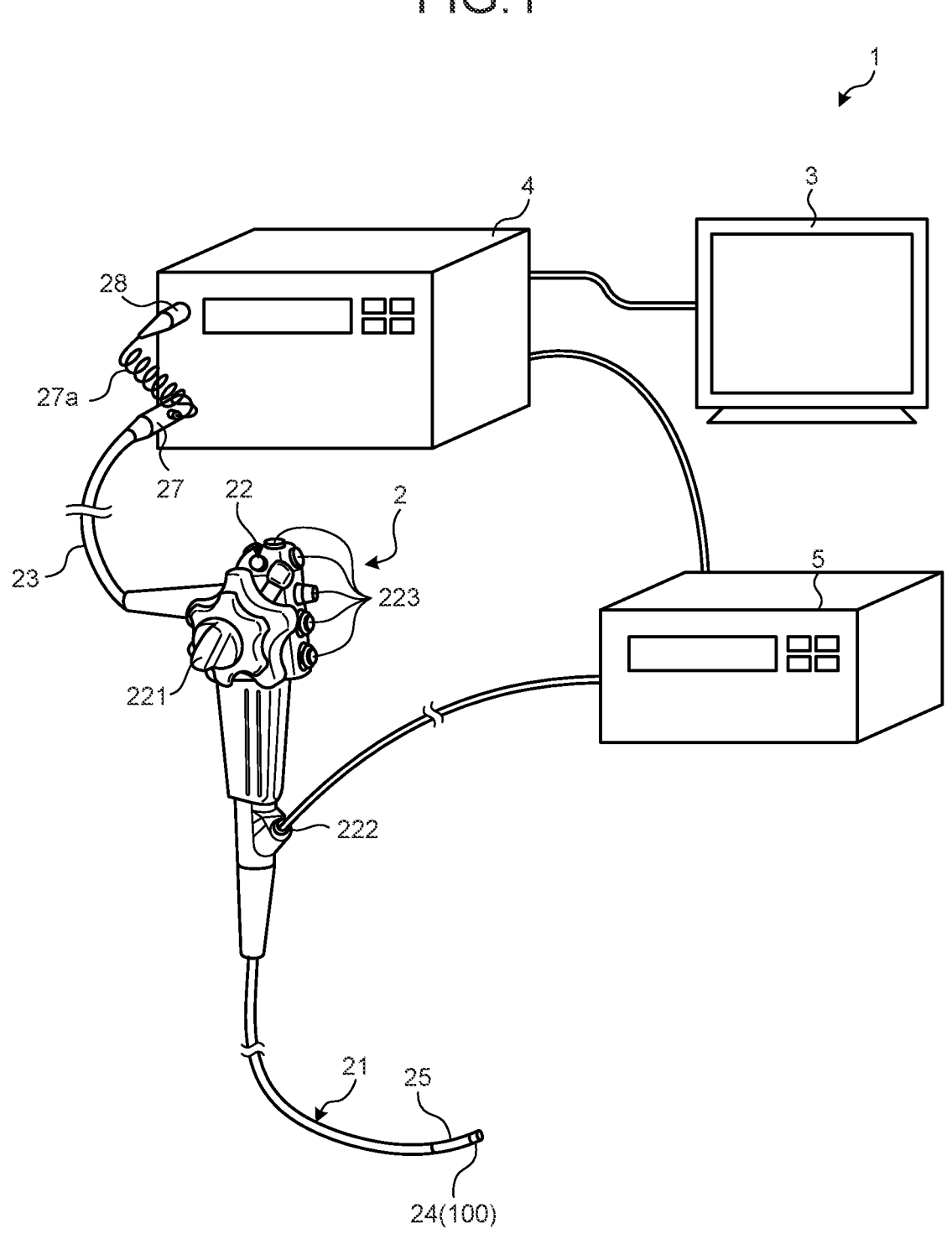
FIG. 1 is a diagram schematically illustrating an entire configuration of an endoscope system according to an embodiment.

An endoscope system using a flexible-scope that is used for transurethral lithotomy ("TUL" below) will be described below as a mode for carrying out the disclosure ("embodiment" below); however, embodiments are not limited thereto. For example, a rigid scope and a surgical robot, or the like, are usable. The embodiment does not limit the disclosure. Furthermore, as for illustration of the drawings, the same components are denoted with the same reference numerals and described. Furthermore, it is necessary to note that the drawings are schematic and the relationship between the thickness and width of each member, the proportion of each member, etc., are different from actual ones. Portions different in mutual sizes and proportions between the drawings may be contained as well.

Configuration of Endoscope System

FIG. 1 is a diagram schematically illustrating an entire configuration of an endoscope system according to an embodiment. An endoscope system 1 illustrated in FIG. 1 captures an internal image of the body of a subject, such as a patient, by inserting an insertion portion of an endoscope into a body cavity or a lumen of the subject, for example, into the urinary tract and displays a display image based on an imaging signal of the captured image on a display device. The urinary tract includes the urethra, the bladder, the ureter and the kidney and has a ductal form extending in a depth direction. A practitioner, such as a doctor, fragments a calculus in the subject with a laser irradiation device that applies a high-power infrared laser, such as a holmium YAG laser, via the endoscope while observing the display image that the display device displays, extracts the fragmented calculus with a treatment tool, such as a basket catheter, and places a medical tool in the urinary tract for a given period. The medical tool is any one of a stent, a catheter, and an indwelling needle. The endoscope system 1 includes an endoscope 2, a display device 3, a control device 4, and a laser irradiation device 5.

Configuration of Endoscope

First of all, a configuration of the endoscope 2 will be described.

The endoscope 2 generates an imaging signal (RAW data) of a captured internal image of the body of the subject and outputs the generated imaging signal to the control device 4. The endoscope 2 includes an insertion portion 21, an operation unit 22, and a universal cord 23.

The insertion portion 21 is inserted into the subject. The insertion portion 21 is flexible and elongated. The insertion portion 21 includes a distal end part 24 that incorporates an imaging device to be described below, a curve part 25 that is formed of multiple curve pieces and that flexibly curves, and a flexible tube 26 that is flexible and elongated and that is connected to a proximal end side of the curve part 25.

The distal end part 24 is configured using glass fibers, etc. The distal end part 24 forms a light guide path for illumination light that is supplied from the control device 4 via the universal cord 23 and the operation unit 22, generates an imaging signal of a captured image of return light of the illumination light, and outputs the imaging signal to the control device 4.

The operation unit 22 includes a curve knob 221 that causes the curve unit 25 to curve in up and down directions and left and right directions, a treatment tool insertion port 222 into which a treatment tool is inserted, and a plurality of switches 223 serving as an operation input unit that, in addition to the control device 4, inputs operation instruction signals to peripherals, such as an air supply unit, a water supply unit and a gas supply unit, a pre-freeze signal of an instruction for the endoscope system 1 to capture a still image, or a switch signal that switches an observation mode of the endoscope system 1. The treatment tool that is inserted from the treatment tool insertion portion 222 goes out of an opening (not illustrated in the drawing) via a treatment tool channel (not illustrated in the drawing) of the distal end part 24. The treatment tool is the laser irradiation device 5, the basket catheter, or the like.

The universal cord 23 incorporates at least a light guide and an assembly cable including a single cable or a bundle of cables. The assembly cable includes a signal line for transmitting and receiving a signal between the endoscope 2 and the control device 4 and for transmitting and receiving the imaging signal (RAW data) and a signal line for transmitting and receiving a drive timing signal (a synchronization signal and a clock signal) for driving the imaging device to be described below. The universal cord 23 includes a connector 27 that is detachable from the control device 4 and a connector 28 to which a coiled coil cable 27a extends and that is detachable from the control device 4 at an end of extension of the coil cable 27a.

Configuration of Display Device

A configuration of the display device 3 will be described next.

The display device 3 displays a display image based on a video signal that is input from the control device 4 under the control of the control device 4. The display device 3 is realized using a display panel of organic electro luminescence (EL), liquid crystals, or the like.

Configuration of Control Device

A configuration of the control device 4 will be described next.

The control device 4 controls each unit of the endoscope system 1. The control device 4 supplies illumination light to be applied to the subject by the endoscope 2. The control device 4 performs various types of image processing on the imaging signal that is input from the endoscope 2 and outputs the processed imaging signal to the display device 3.

Configuration of Laser Irradiation Device

A configuration of the laser irradiation device will be described next.

The laser irradiation device 5 is inserted into the body of the subject, for example, into the urinary tract (for example, the kidney, the ureter, the bladder and the urethra) via the treatment tool insertion portion 222 of the endoscope 2 and, under the operation of the practitioner, applies a high-power infrared laser, such as a holmium YAG laser, to a calculus caused in the subject, thereby fragmenting the calculus.

Functional Configuration of Relevant Part of Endoscope System

Figure 2:
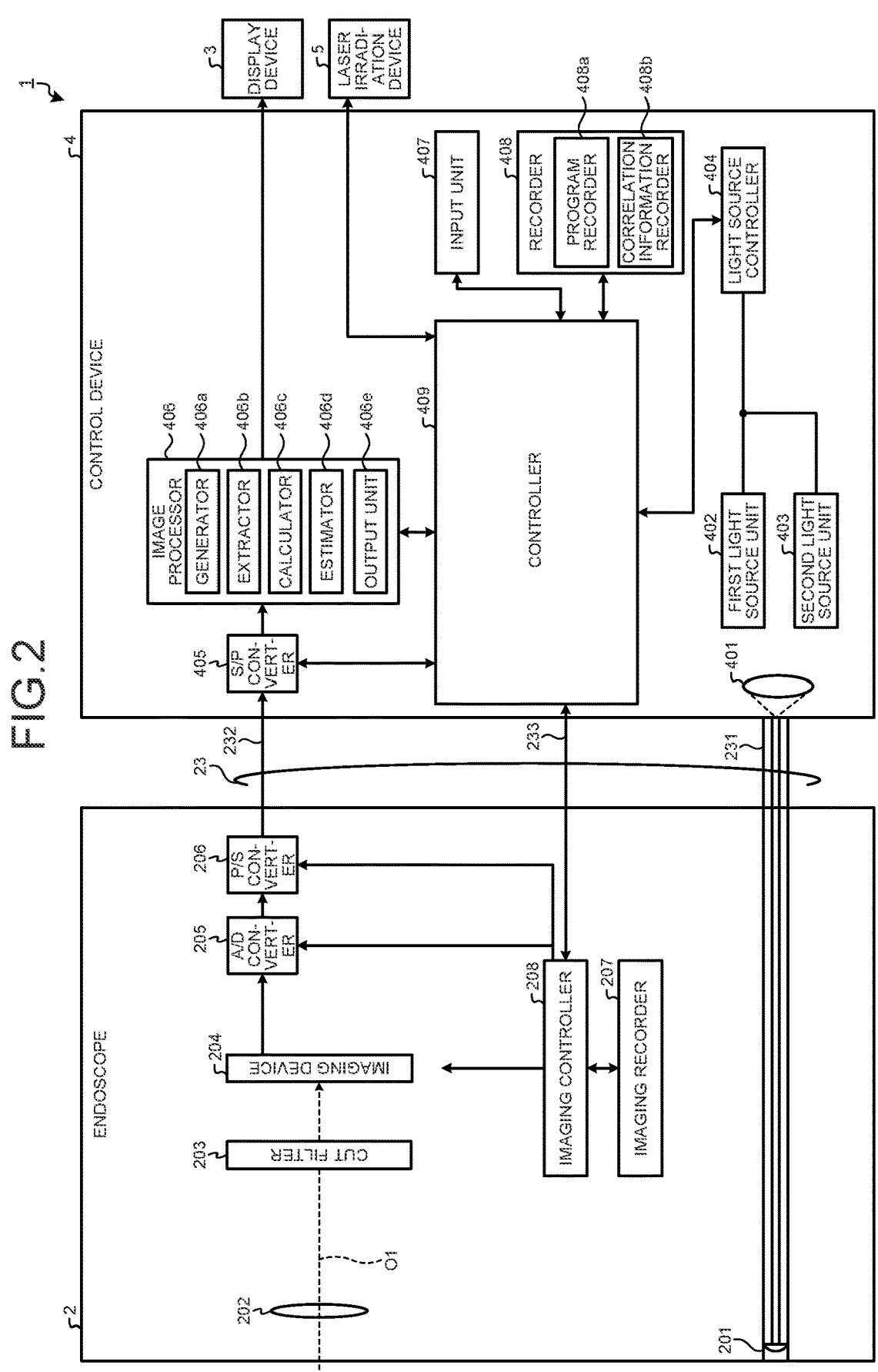
FIG. 2 is a block diagram illustrating a functional configuration of a relevant part of the endoscope system according to the embodiment.

A functional configuration of a relevant part of the endoscope system 1 described above will be described next. FIG. 2 is a block diagram illustrating the functional configuration of the relevant part of the endoscope system 1.

Configuration of Endoscope

First of all, a configuration of the endoscope 2 will be described.

The endoscope 2 includes an illuminating optical system 201, an imaging optical system 202, a cut filter 203, an imaging device 204, an A/D converter 205, a P/S converter 206, an imaging recorder 207, and an imaging controller 208. Note that each of the illuminating optical system 201, the imaging optical system 202, the cut filter 203, the imaging device 204, the A/D converter 205, the P/S converter 206, the imaging recorder 207, and the imaging controller 208 is arranged in the distal end part 24.

The illuminating optical system 201 applies the illumination light that is supplied from a light guide 231 that is formed of optical fibers, etc., to the subject (living tissue). The illuminating optical system 201 is realized using a single lens, a plurality of lenses, or the like.

The imaging optical system 202 focuses light, such as reflection light that is reflected from the subject, return light from the subject, or fluorescence that the subject emits, thereby forming a subject image (ray of light) on a light receiving surface of the imaging device 204. The imaging optical system 202 is realized using a single lens, a plurality of lenses, or the like.

The cut filter 203 is arranged on an optical axis O1 of the imaging optical system 202 and the imaging device 204. The cut filter 203 blocks light having a wavelength band of reflection light or return light of the excitation light that is supplied from the control device 4 to be described below and that is from the subject and transmits light having the wavelength band on a side of wavelengths longer than those of the excitation light. The transmission characteristics of the cut filter 203 will be described below.

Under the control of the imaging controller 208, the imaging device 204 receives the subject image (ray of light) that is formed by the imaging optical system 202 and that is transmitted through the cut filter 203, performs photoelectric conversion to generate imaging signal (RAW data), and outputs the imaging signal to the A/D converter 205. The imaging device 204 is realized using a charge coupled device (CCD) or complementary metal oxide semiconductor (CMOS) image sensor that is formed by arranging any one of color filters forming a Bayer array (RGGB) in each of a plurality of pixels that are formed by being arranged in a two-dimensional matrix.

Under the control of the imaging controller 208, the A/D converter 205 performs the A/D conversion processing on the analog imaging signal that is input from the imaging device 204 and outputs the processed imaging signal to the P/S converter 206. The A/D converter 205 is realized using an A/D conversion circuit, or the like.

Under the control of the imaging controller 208, the P/S converter 206 performs parallel/serial conversion on the digital imaging signal that is input from the A/D converter 205 and outputs the imaging signal on which the parallel/serial conversion has been performed to the control device 4 via a first transmission cable 232. The P/S converter 206 is realized using the P/S conversion circuit, or the like. Note that, according to the first embodiment, an E/O converter that converts an imaging signal into an optical signal may be provided instead of the P/S converter 206 and the imaging signal may be output to the control device 4 using an optical signal and may be transmitted to the control device 4 by wireless communication according to, for example, Wi-Fi (wireless fidelity (trademark).

The imaging recorder 207 records various types of information on the endoscope 2 (for example, pixel information on the imaging device 204 and the characteristics of the cut filter 203). The imaging recorder 207 records various types of setting data and parameters for control that are transmitted from the control device 4 via a second transmission cable 233. The imaging recorder 207 is configured using a non-volatile memory or a volatile memory.

The imaging controller 208 controls operations of each of the imaging device 204, the A/D converter 205, and the P/S converter 206 based on the setting data that is received from the control device 4 via the second transmission cable 233. The imaging controller 208 is realized using a time generator (TG), a processor that is a processing device including hardware, such as a CPU, and a memory that is a temporary storage area that the processor uses.

Configuration of Control Device

A configuration of the control device 4 will be described next.

The control device 4 includes a condenser lens 401, a first light source unit 402, a second light source unit 403, a light source controller 404, a S/P converter 405, an image processor 406, an input unit 407, a recorder 408, and a controller 409.

The condenser lens 401 focuses light that is emitted by each of the first light source unit 402 and the second light source unit 403 and emits the light to the light guide 231. The condenser lens 401 is configured using a single lens or a plurality of lenses.

Under the control of the light source controller 404, the first light source unit 402 emits white light (normal light) that is visible light, thereby supplying white light to the light guide 231. The first light source unit 402 is configured using a white light emitting diode (LED) lamp, a driver, etc. The first light source unit 402 may simultaneously emit light with a red LED lamp, a green LED lamp, and a blue LED lamp, thereby supplying white light that is visible light. Needless to say, the first light source unit 402 may be configured using a halogen lamp or a xenon lamp.

Under the control of the light source controller 404, the second light source unit 403 emits excitation light having a given wavelength band, thereby supplying a narrow-band light as the illumination light to the light guide 231. The excitation light has a wavelength band from 400 nanometers (nm) to 430 nm (the center wavelength is 415 nm). The second light source unit 403 is realized using a collimating lens, a semiconductor laser, such as a violet laser diode (LD), a driver, etc. The wavelength characteristics of each of the white light that is emitted by the first light source unit 402 and the excitation light that is emitted by the second light source unit 403 will be described below.

The light source controller 404 is configured using a processor that is a processing device including hardware, such as a field programmable agate array (FPGA) or a CPU, and a memory that is a temporary storage area that the processor uses. The light source controller 404 controls light emission timing, the light emission intensity and the light emission time, etc., of each of the first light source unit 402 and the second light source unit 403.

Under the control of the controller 409, the S/P converter 405 performs serial/parallel conversion on the imaging signal that is received from the endoscope 2 via the first transmission cable 232 and outputs the processed imaging signal to the image processor 406. Note that, in the case where the endoscope 2 outputs the imaging signal in an optical signal, an O/E converter that converts the optical signal into an electric signal may be provided instead of the S/P converter 405. In the case where the endoscope 2 transmits the imaging signal by wireless communication, a communication module capable of receiving a radio signal may be provided instead of the S/P converter 405.

The image processor 406 is realized using a processor including hardware, such as a CPU, a graphics processing unit (GPU) or a FPGA, and a memory that is a temporary storage area that the processor uses. Under the control of the controller 409, the image processor 406 performs given image processing on the imaging signal that is input from the S/P converter 405 and outputs the processed imaging signal to the display device 3. Note that, in the embodiment, the image processor 406 functions as an assist device. The image processor 406 includes a generator 406a, a calculator 406c, an extractor 406b, an estimator 406d, and an output unit 406e.

The generator 406a generates a fluorescence image based on the imaging signal that is generated by capturing an image of fluorescence caused by the excitation light that is applied to living tissue. Specifically, the generator 406a acquires the imaging signal from the imaging device 204 of the endoscope 2 via the A/D converter 205, the P/S converter 206, the first transmission cable 232, and the S/P converter 405 (simply described as "acquires from the imaging device 204 of the endoscope 2" below). The generator 406a generates a fluorescence image based on the imaging signal that is acquired from the imaging device 204 of the endoscope 2 and that is generated by capturing an image of the fluorescence caused by the excitation light that is applied to the living tissue. The generator 406a generates an observation image (white light image) that is a display image based on an imaging signal that is generated by imaging the reflection light that is reflected from the living tissue because of application of white light to the living tissue and the return light.

The extractor 406b extracts a fluorescence area from the fluorescence image. Specifically, the extractor 406b extracts a fluorescence area by performing a binary process on each pixel of the fluorescence image. For example, the extractor 406b extracts a fluorescence area by extracting pixels of the fluorescence image whose pixel values are equal to or larger than a given value.

The calculator 406c calculates a fluorescence intensity based on the fluorescence image that is generated by the generator 406a. Specifically, the calculator 406c calculates a fluorescence intensity of the fluorescence area that is the fluorescence image generated by the generator 406a and that is extracted by the extractor 406b.

The estimator 406d estimates a placement period during which a medical tool is placed in a lumen based on the fluorescence intensity that is calculated by the calculator 406c. The lumen is the urinary tract here. The urinary tract includes the urethra, the bladder, the ureter and the kidney. The medical tool is any one of a stent, a catheter, and an indwelling needle. The estimator 406d estimates a degree of invasion of living tissue with an energy device based on the fluorescence intensity that is calculated by the calculator 406c and, based on the degree of invasion, estimates the period during which the medical tool is placed. Specifically, the estimator 406d estimates a degree of invasion of living tissue with the energy device based on correlation information representing a correlation between the degree of invasion and the fluorescence intensity that a correlation information recorder 408b to be described below records and the fluorescence intensity that is calculated by the calculator 406c.

The output unit 406e outputs placement period information on the placement period for the medical tool that is estimated by the estimator 406d and the observation image serving as the display image obtained by capturing an image of the living tissue to the display device 3.

The input unit 407 receives inputs of various types of operations on the endoscope system 1 and outputs the received operations to the controller 409. The input unit 407 is configured using a mouse, a foot switch, a keyboard, a button, a switch, a touch panel, etc.

The recorder 408 is realized using a volatile memory, a non-volatile memory, a solid state drive (SSD) or a hard disk drive (HDD) or a recording medium, such as a memory card. The recorder 408 records data containing various types of parameters necessary for operations of the endoscope system 1. The recorder 408 includes a program recorder 408a that records various types of programs for running the endoscope system 1 and the correlation information recorder 408b.

The correlation information recorder 408b records the degree of invasion of the living tissue of the subject with the laser irradiation device 5 and the intensity of fluorescence that is emitted when excitation light is applied to the living tissue that is thermally treated by the laser irradiation device 5. Details of the correlation information will be described below.

The controller 409 is realized using a processor including hardware, such as a FPGA or a CPU, and a memory that is a temporary storage area that the processor uses. The controller 409 generally controls each of the units forming the endoscope system 1.

Wavelength Characteristics of Excitation Light

Wavelength characteristics of excitation light that is emitted by the second light source unit 403 will be described next.

Figure 3:
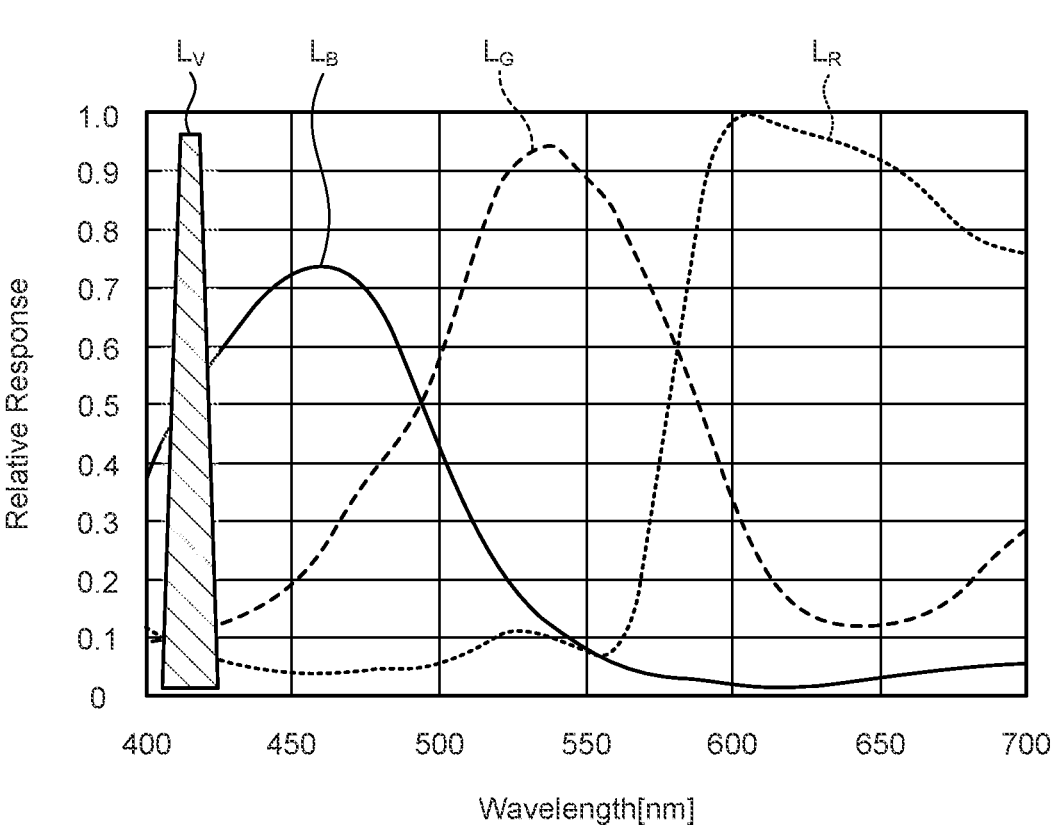
FIG. 3 is a diagram schematically illustrating wavelength characteristics of excitation light that a second light source unit emits according to the embodiment.

FIG. 3 is a diagram schematically illustrating the wavelength characteristics of the excitation light that the second light source unit 403 emits. In FIG. 3, the horizontal axis represents the wavelength (nm) and the vertical axis represents the wavelength characteristics. In FIG. 3, the polygonal chain $L_V$ represents the wavelength characteristic of the excitation light that is emitted by the second light source unit 403. In FIG. 3, the curve $L_B$ represents the wavelength band of blue, the curve $L_G$ represents the wavelength band of green, and the curve $L_R$ represents the wavelength band of red.

As illustrated in FIG. 3, the second light source unit 403 emits the excitation light having a center wavelength (peak wavelength) of 415 nm and a wavelength band from 400 to 430 nm.

Transmission Characteristics of Cut Filter

The transmission characteristics of the cut filter 203 will be described next.

Figure 4:
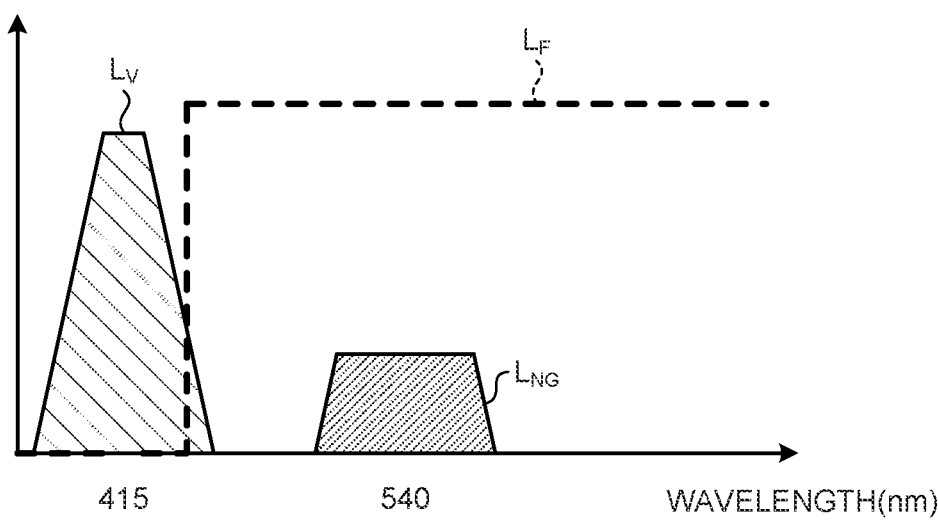
FIG. 4 is a diagram schematically illustrating transmission characteristics of a cut filter according to the embodiment.

FIG. 4 is a diagram schematically illustrating the transmission characteristics of the cut filter 203. In FIG. 4, the horizontal axis represents the wavelength (nm) and the vertical axis represents the transmission characteristics. In FIG. 4, the polygonal chain $L_F$ represents the transmission characteristic of the cut filter 203, the polygonal chain $L_V$ represents the wavelength characteristics of the excitation light, and the polygonal chain $L_{NG}$ represents the wavelength characteristics of fluorescence caused by application of the excitation light to advanced glycation end products caused by thermal treatment on living tissue performed by an energy device, for example, the laser irradiation device 5.

As represented by the polygonal chain $L_V$ and the polygonal chain $L_{NG}$, the cut filter 203 blocks part of the excitation light that is reflected from the living tissue of the observation area and transmits light having another wavelength band containing fluorescence components. Specifically, the cut filter 203 blocks part of the light having a wavelength band on a short-wavelength side from 400 nm and under 430 nm containing the excitation light and transmits light having a wavelength band on a long wavelength side from 430 nm containing fluorescence caused by application of the excitation light to the advanced glycation end products caused by the thermal treatment.

Correlation Information

An example of the correlation information that the correlation information recorder 408*b* records will be described next.

Figure 5:
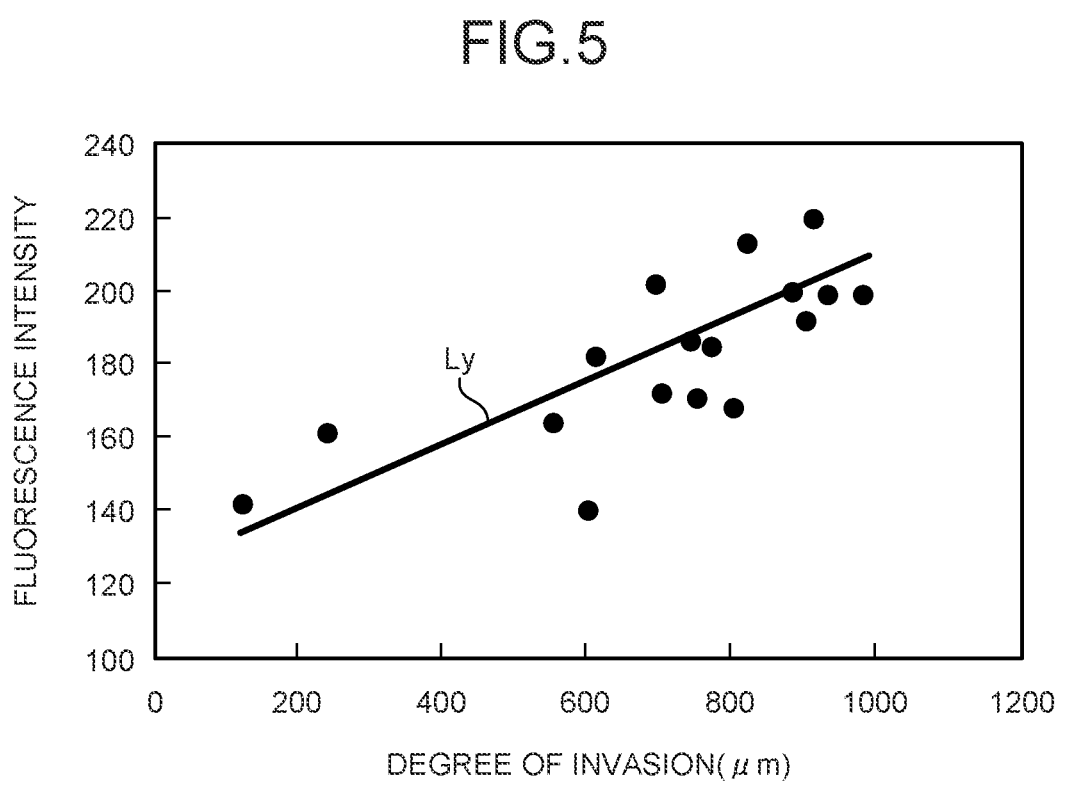

FIG. 5 is a diagram illustrating an example of the correlation information that the correlation information recorder 408*b* records. In FIG. 5, the vertical axis represents the light emission intensity and the horizontal axis represents the degree of invasion (the depth and the area) of living tissue by thermal treatment. In FIG. 5, the straight line Ly represents the correlation between the light emission intensity and the degree of invasion (depth and area) to the living tissue by thermal treatment.

As represented by the straight line Ly in FIG. 5, the larger the degree of invasion of living tissue by thermal treatment is, the higher the light emission intensity is.

Overview of Fluorescence Observation Mode

Figure 6:
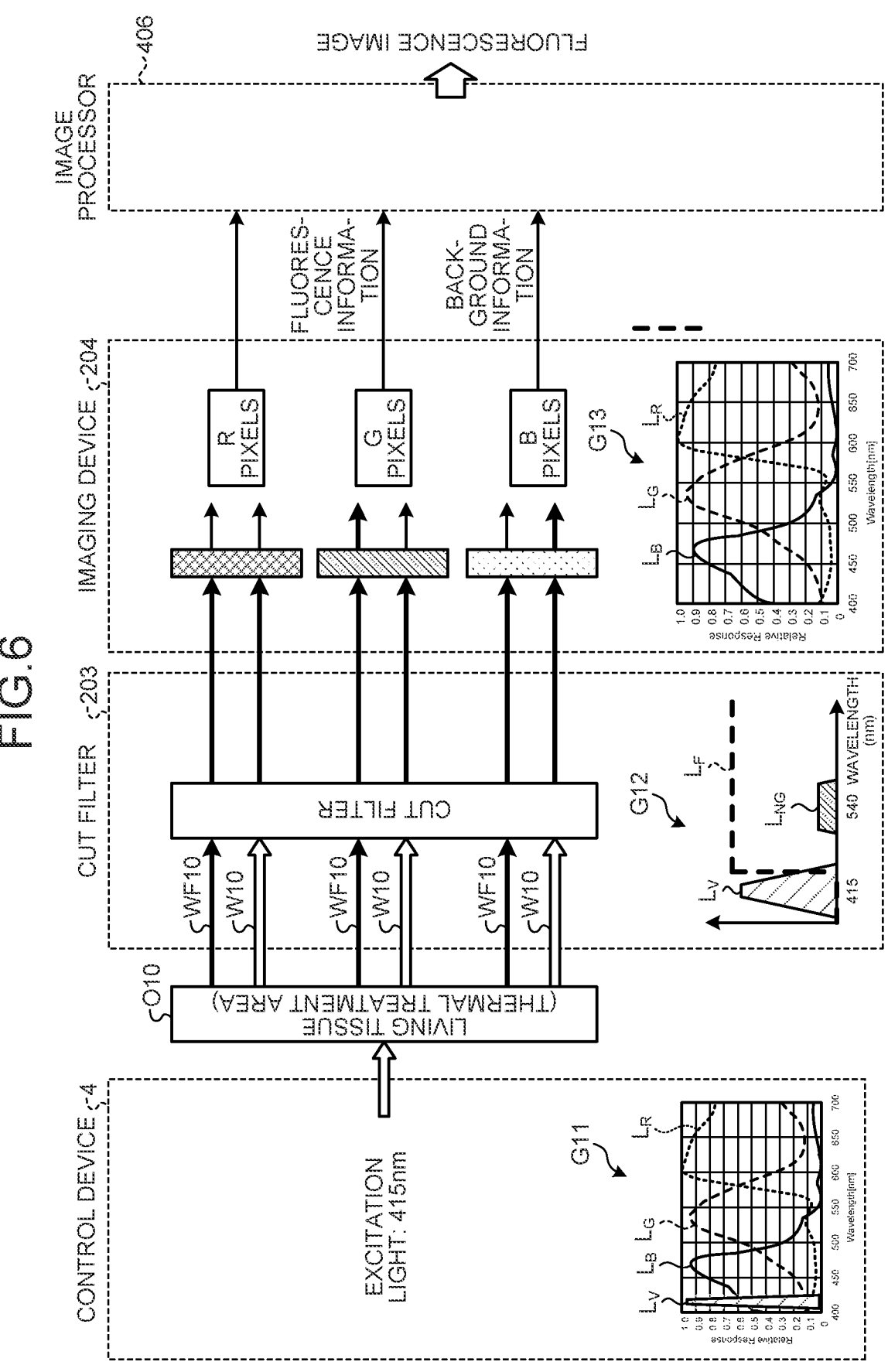
FIG. 6 is a diagram schematically illustrating a principle of observation in a fluorescence observation mode of the endoscope system according to the embodiment.

A fluorescence observation mode (thermal treatment observation mode) that is executable in the endoscope system 1 will be described next. FIG. 6 is a diagram schematically illustrating a principle of observation in the fluorescence observation mode.

As represented in the graph G11 in FIG. 6, first of all, the control device 4 causes the second light source unit 403 to emit light, thereby applying the excitation light (having a center wavelength of 415 nm) to the living tissue O10 (thermal treatment area) resulting from thermal treatment performed by the laser irradiation device 5 on the subject. In this case, as represented in the graph G12 in FIG. 6, while the reflection light containing at least the components and the return light that is reflected on the living tissue O10 (the thermal treatment area) (simply referred to as "reflection light W10" below) is blocked by the cut filter 203 and the intensity of the reflection light lowers, part of the components on a side of wavelengths longer than that of the wavelength band that is mostly blocked is incident on the imaging device 204 with its intensity not lowering.

More specifically, as represented in the graph G12 in FIG. 6, the cut filter 203 blocks most of the reflection light W10 that is incident on the G pixels and that has a wavelength band of short wavelengths containing the wavelength band of the excitation light and transmits the wavelength band on a side of wavelengths longer than that of the wavelength band that is mostly blocked. Furthermore, as represented in the graph G12 in FIG. 6, the cut filter 203 transmits fluorescence (WF10) that is emitted by the self-luminous AGEs in the living tissue O10 (thermal treatment area). Thus, the reflected light W1 with the lower intensity and the fluorescence (WF10) are incident on each of the R pixels, the G pixels and the B pixels.

As represented by the polygonal chain $L_{NG}$ of fluorescence characteristics in the graph G12 in FIG. 6, the G pixels have sensitivity to fluorescence; however, because of a very small response to fluorescence, the output value is a small value.

Thereafter, the image processor 406 acquires an imaging signal (RAW data) from the imaging device 204 of the endoscope 2 and performs image processing on each of the signal values of the G pixels and the B pixels contained in the acquired imaging signal, thereby generating a fluorescence image. In this case, the signal values of the G pixels contain fluorescence information. The B pixels contain background information from the living tissue of the subject containing the thermal treatment area. In this case, the image processor 406 generates a fluorescence image by performing demosaicing, processing of calculating a ratio of intensities of the respective pixels, processing of determining a fluorescence area and a background area, and image processing using different parameters on each of color component signals (pixel values) of pixels positioned in the fluorescence area and each of color component signals (pixel values) of pixels positioned in the background area. The image processor 406 outputs the fluorescence image to the display device 3. The fluorescence area is an area where the fluorescence information is more dominant than the background information. The background area is an area where the background information is more dominant than the fluorescence information. Specifically, the extractor 406*b* in the image processor 93 extracts the fluorescence area and the background area by, while determining that it is a fluorescence area when the intensity ratio of a reflection light component signal corresponding to the background information contained in the pixels and the fluorescence component signal corresponding to the fluorescence information is at or above a given threshold (for example, 0.5 or more), determining that it is a background area when the intensity ratio is under the given threshold.

As described above, the fluorescence observation mode (thermal treatment observation mode) makes it possible to easily observe the living tissue that is thermally treated by the laser irradiation device 5 (thermal treatment area).

Overview of Normal Observation Mode

Figure 7:
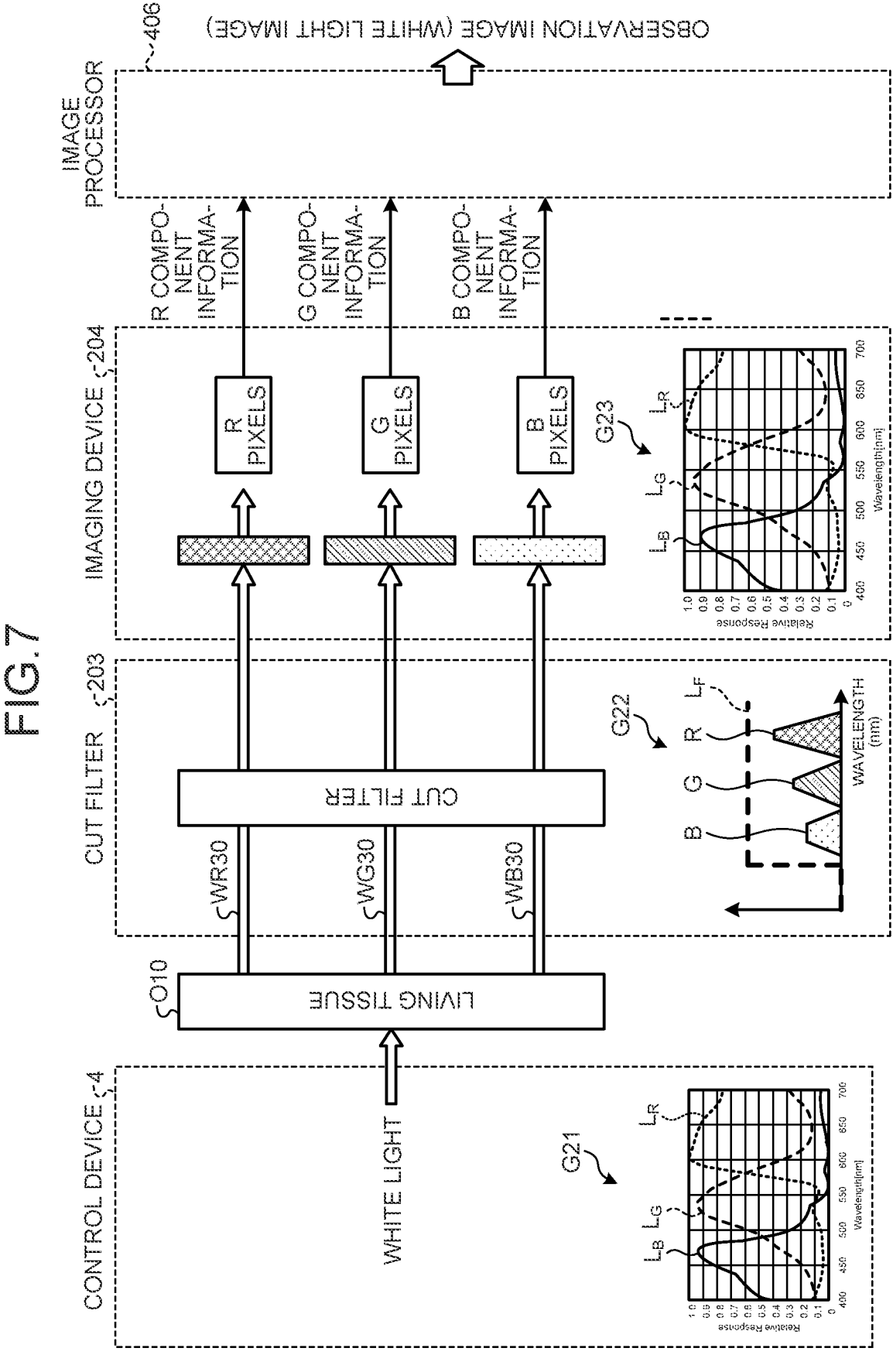
FIG. 7 is a diagram schematically illustrating a principle of observation in a normal observation mode of the endoscope system according to the embodiment.

A normal light observation mode that is executable by the endoscope system 1 will be described next. FIG. 7 is a diagram schematically illustrating a principle of observation in the normal light observation mode.

As illustrated in FIG. 7, first of all, the control device 4 causes the first light source unit 402 to emit light, thereby applying white light W3 to the living tissue O10. In this case, part of reflection light and return light (simply referred to as "reflection light WR30, reflection light WG30, and reflection light WB30" below) that are reflected on the living tissue O10 is blocked by the cut filter 203 and the rest is incident on the imaging device 204. Specifically, as illustrated in FIG. 7, the cut filter 203 blocks the reflection light having the wavelength band of short wavelengths containing the wavelength band of narrow-band light. For this reason, as illustrated in FIG. 7, the components of light having the wavelength band of blue that is incident on the B pixels are less than those in the case where the cut filter 203 is not arranged.

Thereafter, the image processor 406 acquires an imaging signal (RAW data) from the imaging device 204 and performs image processing on each of the signal values of the R pixels, the G pixels and the B pixels contained in the acquired imaging signal, thereby generating an observation image (white light image) that is a display image. In this case, because the blue components contained in the imaging signal are less than those in conventional white light observation, the image processor 406 performs white balance adjustment processing of adjusting white balance such that the ratio of red components, green components, and blue components is constant.

As described above, the normal observation mode makes it possible to observe a natural observation image (white image) even when the cut filter 203 is arranged.

Manipulation Method of Flexible Transurethral Lithotomy Using Endoscope System

Figure 8:
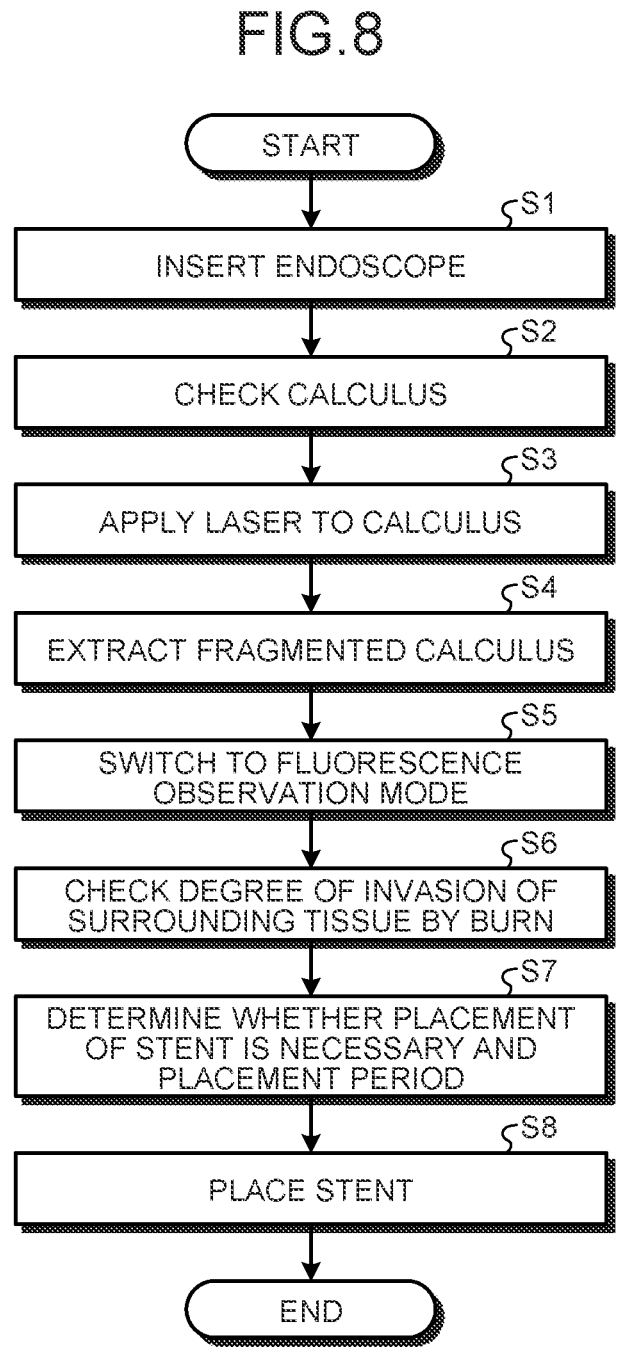
FIG. 8 is a flowchart illustrating a manipulation method of flexible transurethral lithotomy performed by a practitioner using the endoscope system.

A manipulation method of flexible transurethral lithotomy (f-TUL) performed by a practitioner using the endoscope system 1 will be described next. FIG. 8 is a flowchart illustrating a manipulation method of flexible transurethral lithotomy (f-TUL) performed by a practitioner using the endoscope system 1. FIGS. 9A to 9F are diagrams illustrating transition of the image that the display device 3 displays in flexible transurethral lithotomy f-TUL).

Figure 9A:
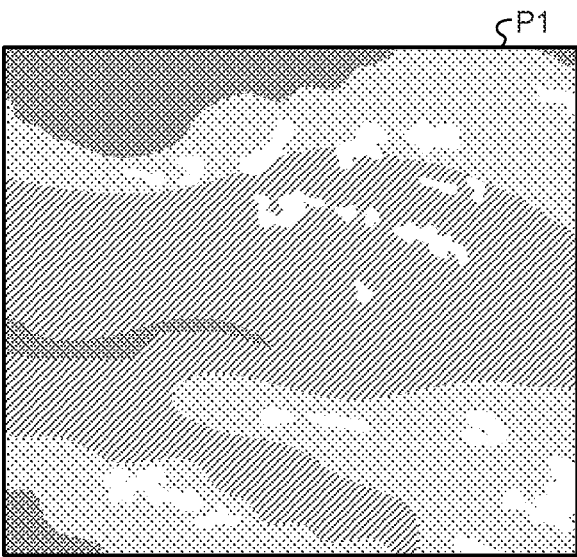
FIG. 9A is a diagram illustrating an example of transition in an image that a display device displays in flexible transurethral lithotomy.

As illustrated in FIG. 8, first of all, the practitioner inserts the insertion portion 21 of the endoscope 2 into the urinary tract (ureter) of a subject while applying white light (normal light) (step S1). In this case, as illustrated in FIG. 9A, the practitioner inserts the insertion portion 21 of the endoscope 2 into the urinary tract of the subject while observing an observation image P1 resulting from the white light and displayed on the display device 3.

Figure 9B:
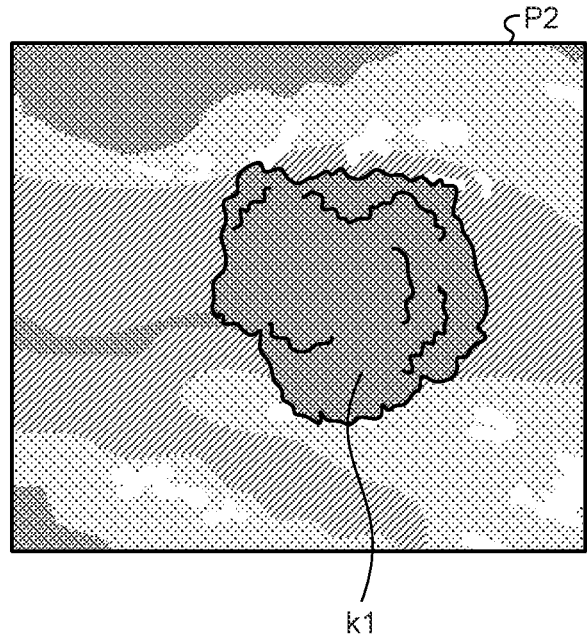
FIG. 9B is a diagram illustrating an example of the transition in the image that the display device displays in flexible transurethral lithotomy.

Subsequently, while viewing the observation image P1 that is displayed on the display device 3, the practitioner checks a calculus that is caused in the subject (step S2). In this case, as illustrated in FIG. 9B, the practitioner checks the size and the position of a calculus K1 while observing the observation image P2 displayed on the display device 3 and inserting the insertion portion 21 of the endoscope 2 into the urinary tract of the subject and while searching for the calculus K1.

Figure 9C:
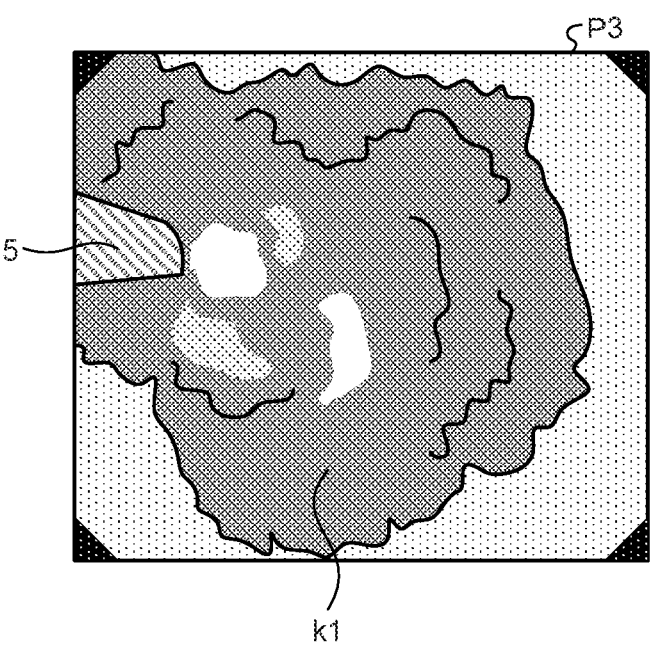
FIG. 9C is a diagram illustrating an example of the transition in the image that the display device displays in flexible transurethral lithotomy.

Thereafter, while viewing the observation image that is displayed on the display device 3, the practitioner inserts the laser irradiation device 5 into the ureter of the subject via the treatment tool insertion portion 222 of the endoscope 2 and applies a laser to the calculus (step S3). In this case, as illustrated in FIG. 9C, the practitioner fragments the calculus K1 by applying a laser with the laser irradiation device 5 to the calculus K1 while observing the observation image P3 that is displayed on the display device 3.

Figure 9D:
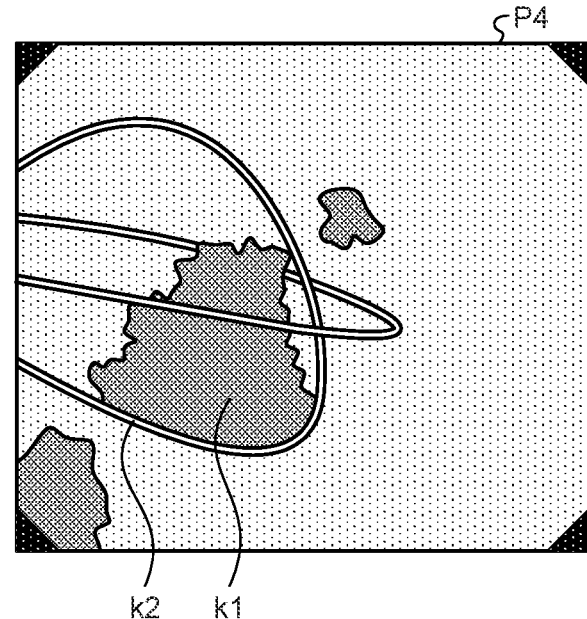
FIG. 9D is a diagram illustrating an example of the transition in the image that the display device displays in flexible transurethral lithotomy.
Figure 9E:
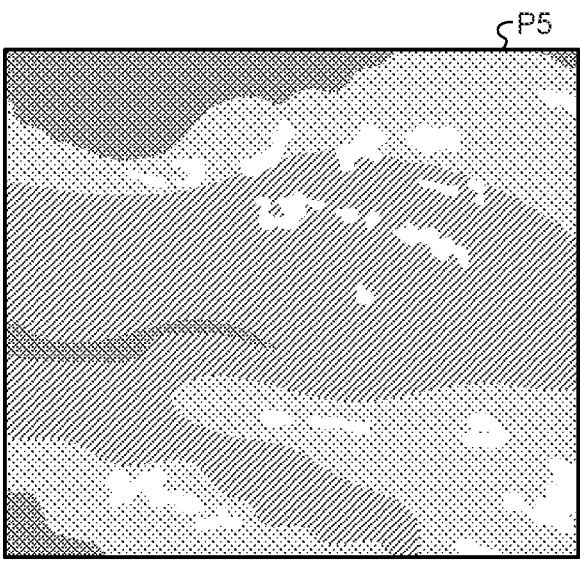
FIG. 9E is a diagram illustrating an example of the transition in the image that the display device displays in flexible transurethral lithotomy.

Subsequently, while viewing the observation image that is displayed on the display device 3, the practitioner extracts the fragmented calculus from the subject with a basket via the treatment tool insertion portion 222 of the endoscope 2 (step S4). In this case, as illustrated in FIGS. 9D and 9E, while viewing an observation image P4 or an observation image P5, the practitioner extracts the fragmented calculus K1 that is fragmented with a treatment tool that can be gripped, for example, a basket catheter K2 via the treatment tool insertion portion 222 of the endoscope 2.

Figure 9F:
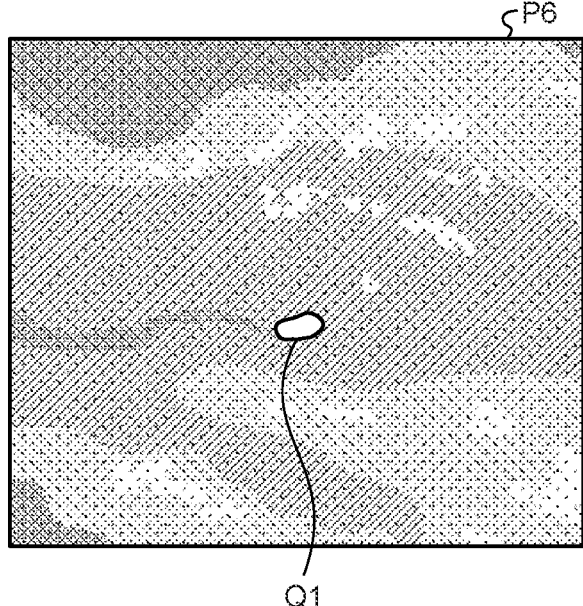
FIG. 9F is a diagram illustrating an example of the transition in the image that the display device displays in flexible transurethral lithotomy.

Thereafter, the practitioner switches the observation mode in which the endoscope 2 performs irradiation from the normal light observation mode to the fluorescence observation mode (a thermal treatment observation mode) by operating the operation unit of the endoscope 2 (step S5). In this case, by causing the second light source unit 403 to emit light, the control device 4 applies excitation light to the subject. As illustrated in FIG. 9F, by observing a fluorescence area Q1 contained in a fluorescence image P6 that is displayed on the display device 3, the practitioner knows a degree of invasion by a burn caused by the laser irradiation device 5.

Subsequently, the practitioner knows the degree of invasion of surrounding tissue by a burn caused by the laser irradiation device 5 while switching the observation mode of the endoscope 2 between the fluorescence observation mode and the normal light observation mode alternately by operating the operation unit 22 of the endoscope 2 (step S6).

Thereafter, while referring to whether it is necessary to place a stent and a placement period that the display device 3 displays, the practitioner determines placement of a stent and a placement period (step S7). In this case, based on the light emission intensity of a light emission area contained in the fluorescence image P6, the control device 4 outputs placement period information on whether it is necessary to place a stent in the urinary tract and on the placement period onto the observation image that is displayed on the display device 3. Accordingly, with reference to the placement period information that is displayed on the display device 3, the practitioner determines whether it is necessary to place a stent in the urinary tract and a placement period. Note that a method of making an estimation on whether it is necessary to place a stent in the urinary tract and on a placement period that the control device 4 causes the display device 3 to display will be described below.

Subsequently, when a stent is placed in the urinary tract, the practitioner places a stent in the urinary tract (step S8). Thereafter, the practitioner pulls the endoscope 2 out of the urinary tract of the subject and ends manipulation.

As described, after fragmenting a calculus that is positioned in the urinary tract of a subject by a laser and extracting the fragmented calculus from the subject with a treatment tool, or the like, the practitioner switches the observation mode of the endoscope system 1 from the normal light observation mode to the fluorescence observation mode and knows the degree of invasion of living tissue of the subject by the laser, thereby determining whether it is necessary to place a stent and a placement period.

Process Executed by Endoscope System

A process that the endoscope system 1 executes will be described next.

Figure 10:
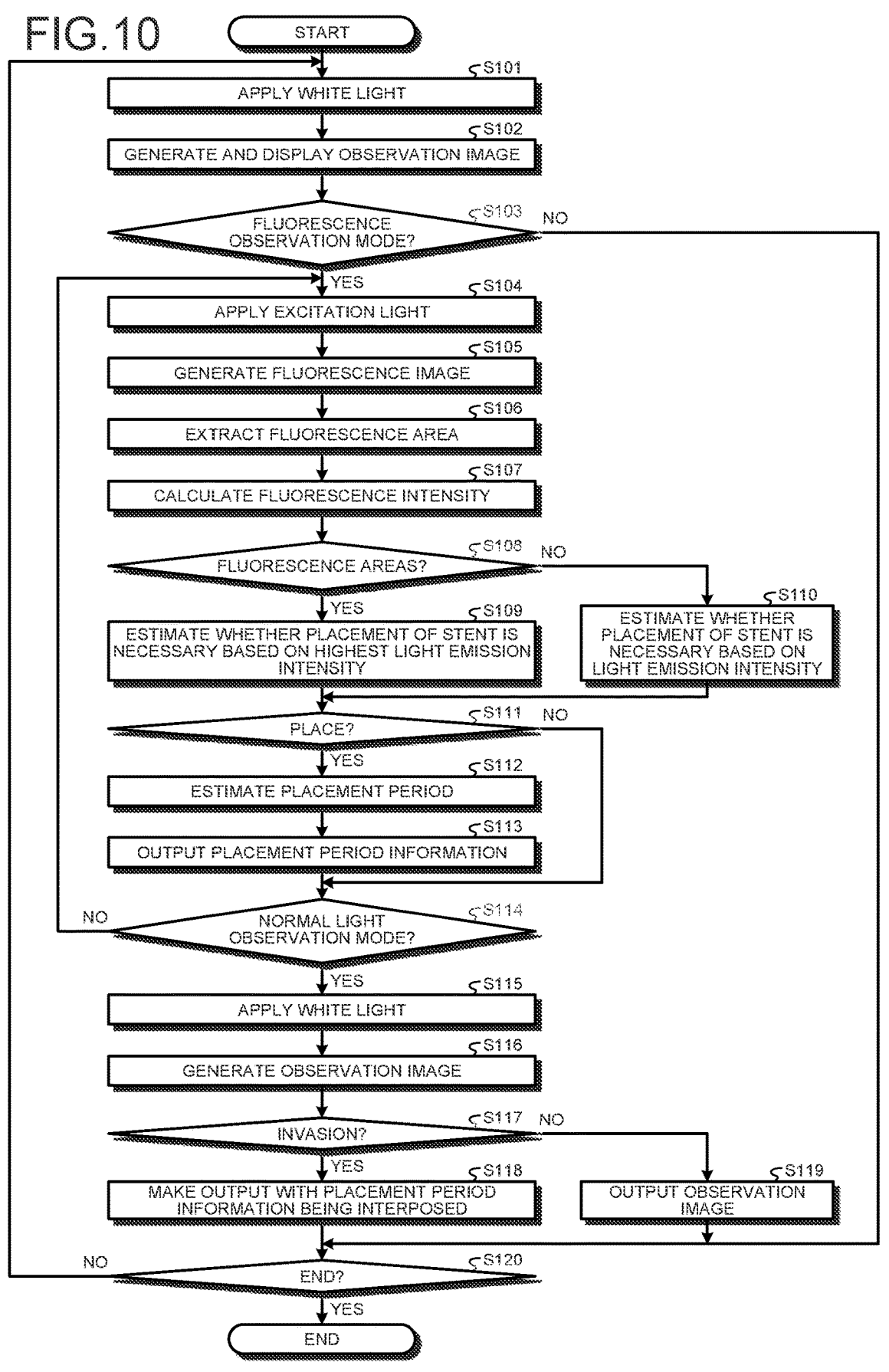
FIG. 10 is a flowchart illustrating an overview of a process that an endoscope system according to the embodiment executes.

FIG. 10 is a flowchart illustrating an overview of the process executed by the endoscope system 1.

As illustrated in FIG. 10, first of all, the controller 409 causes the first light source unit 402 to emit light by controlling the light source controller 404, thereby applying white light to a subject (step S101).

Subsequently, the image processor 406 acquires an imaging signal from the imaging device 204 of the endoscope 2, generates an observation image that is a display image, and outputs the observation image to the display device 3 (step S102).

Thereafter, the controller 409 determines whether a change signal that changes the observation mode to the fluorescence observation mode is input from the input unit 407 or the operation unit 22 of the endoscope 2 (step S103). When the controller 409 determines that the change signal that changes the observation mode to the fluorescence observation mode is input from the input unit 407 or the operation unit 22 of the endoscope 2 (YES at step S103), the endoscope system 1 moves to step S104 described below. On the other hand, when the controller 409 determines that the change signal that changes the observation mode to the fluorescence observation mode is not input from the input unit 407 or the operation unit 22 of the endoscope 2 (NO at step S103), the endoscope system 1 moves to step S120 described below.

At step S104, the controller 409 causes the second light source unit 403 to emit excitation light by controlling the light source controller 404.

Subsequently, the image processor 406 generates a fluorescence image based on the imaging signal that is generated by the imaging device 204 of the endoscope 2 (step S105).

Thereafter, the extractor 406b extracts a fluorescence area that is contained in the fluorescence image that is generated by the generator 406a (step S106). Specifically, the extractor 406b extracts a fluorescence area by performing the binary process, or the like, on the fluorescence image. When a plurality of fluorescence areas are contained in the fluorescence image, the extractor 406b extracts the fluorescence areas.

Subsequently, the calculator 406c calculates a fluorescence intensity of the fluorescence area that is extracted by the extractor 406b (step S107). In this case, when the extractor 406b extracts a plurality of fluorescence areas, the calculator 406c calculates fluorescence intensities of the respective fluorescence areas.

Subsequently, the estimator 406d determines whether there are a plurality of fluorescence areas (step S108). When the estimator 406d determines that there are a plurality of fluorescence areas (YES at step S108), the endoscope system 1 moves to step S109 described below. On the other hand, when the estimator 406d determines that there are not a plurality of fluorescence areas (NO at step S108), the endoscope system 1 moves to step S110 described below.

Figure 11:
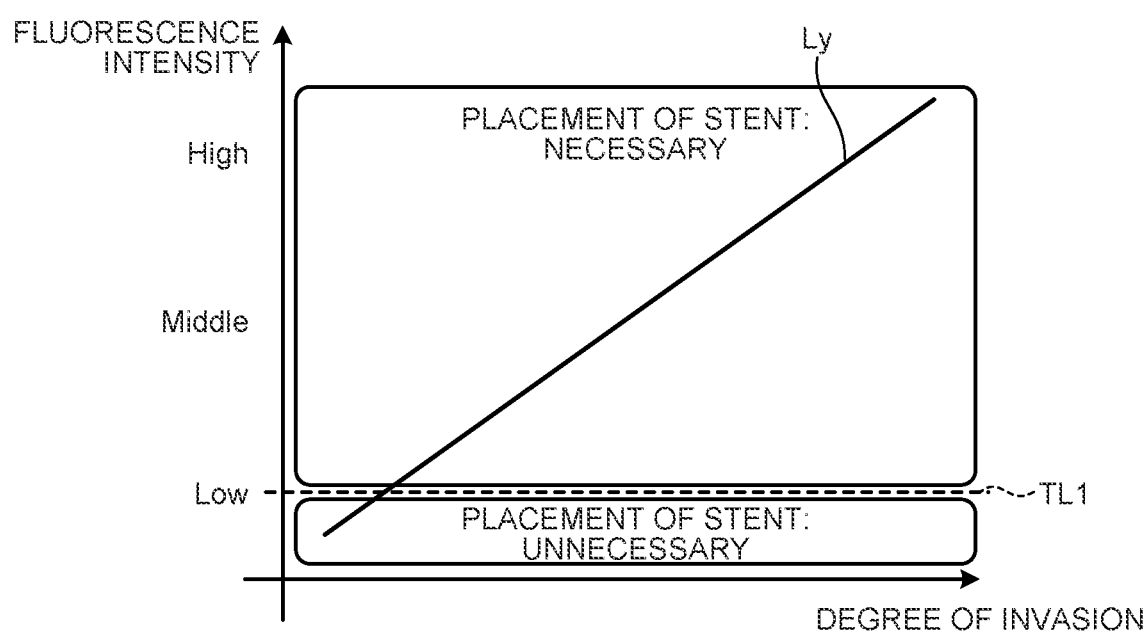
FIG. 11 is a diagram schematically illustrating a method of making an estimation on whether to place a stent that is performed by an estimation unit of the endoscope system according to the embodiment.

At step S109, the estimator 406d makes an estimation on whether to place a stent in the urinary tract based on the highest light emission intensity among those of the fluorescence areas that are calculated by the calculator 406c and correlation information that the correlation information recorder 408b records. Specifically, as illustrated in FIG. 11, the estimator 406d makes an estimation on whether to place a stent in the urinary tract based on the correlation information that is recorded in the correlation information recorder 408b and the light emission intensity that is calculated by the calculator 406c. For example, as illustrated in FIG. 11, the estimator 406d determines whether the light emission intensity is under a threshold TL1 representing a value indicating that it is unnecessary to place a stent based on the correlation information that is recorded by the correlation information recorder 408b and the light emission intensity that is calculated by the calculator 406c and, when the light emission intensity is under the threshold TL1, estimates that it is unnecessary to place a stent in the urinary tract. On the other hand, when the light emission intensity is at or above the threshold TL1 according to the correlation information that is recorded by the correlation information recorder 408b and the light emission intensity that is calculated by the calculator 406c, the estimator 406d estimates that it is necessary to place a stent in the urinary tract. After step S109, the endoscope system 1 moves to step S111 described below.

At step S110, the estimator 406d makes an estimation on whether it is necessary to place a stent based on the light emission intensity that is calculated by the calculator 406c and the correlation information that is recorded by the correlation information recorder 408b. After step S110, the endoscope system 1 moves to step S111 described below.

At step S111, when the estimator 406d estimates placement of a stent in the urinary tract (YES at step S111), the endoscope system 1 moves to step S112 described below. On the other hand, when the estimator 406d estimates placement of no stent in the urinary tract (NO at step S111), the endoscope system 1 moves to step S114 described below.

Figure 12:
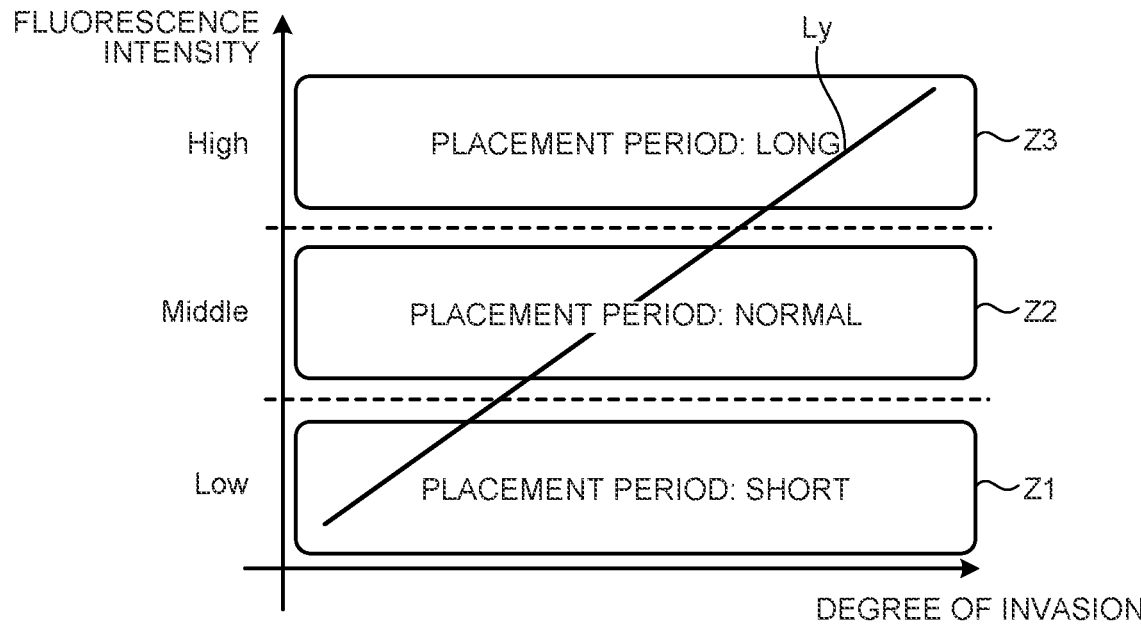
FIG. 12 is a diagram schematically illustrating a method of, by the estimator of the endoscope system, estimating a period during which a stent is placed according to the embodiment.

At step S112, the estimator 406d estimates a period during which a stent is placed in the urinary tract based on the light emission intensity that is calculated by the calculator 406c and the correlation information that is recorded in the correlation information recorder 408b. Specifically, as illustrated in FIG. 12, the estimator 406d estimates a period during which a stent is placed in the urinary tract based on the light emission intensity that is calculated by the calculator 406c and the correlation information that is recorded by the correlation information recorder 408b. For example, as illustrated in FIG. 12, the estimator 406d estimates that a placement period for a stent is short when the correlation between the light emission intensity and the degree of invasion is positioned in a first zone Z1 (Low) according to the light emission intensity that is calculated by the calculator 406c and the correlation information that is recorded by the correlation information recorder 408b, estimates that a placement period for a stent is normal when the correlation between the light emission intensity and the degree of invasion is positioned in a second zone Z2 (middle), and estimates that a placement period for a stent is long when the correlation between the light emission intensity and the degree of invasion is positioned in a third zone Z3 (high). The short period here is about few days, the normal period is about a week, and the long period is 10 days or more.

Figure 13:
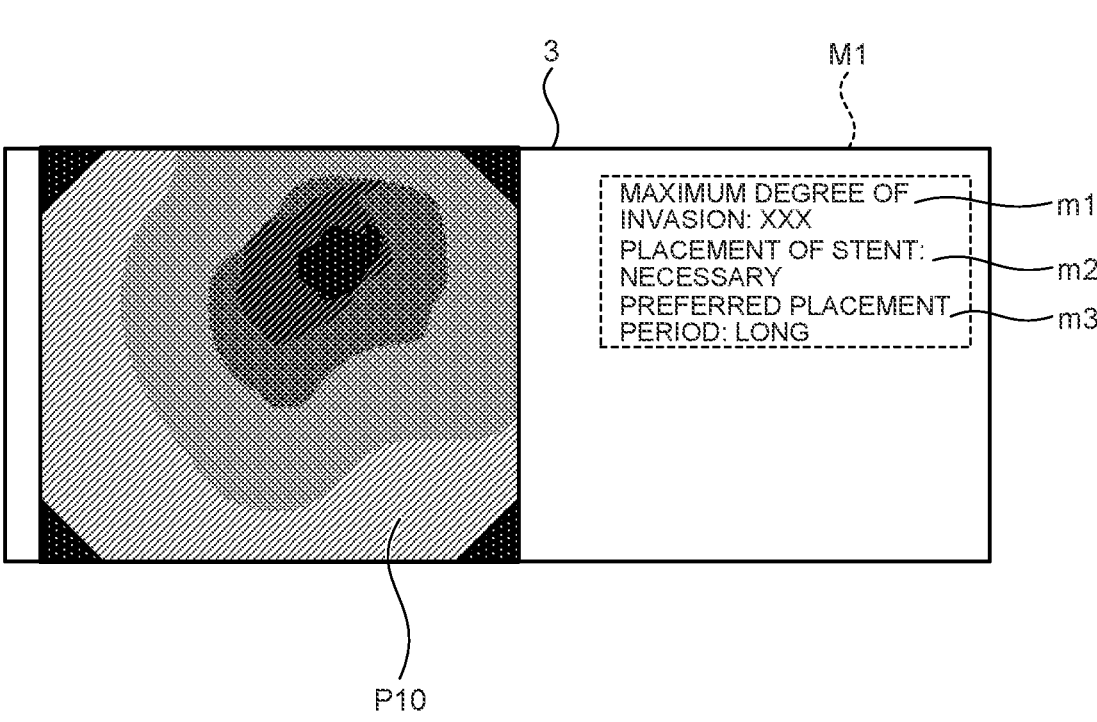
FIG. 13 is a diagram illustrating an example of an output screen that an output unit of the endoscope system outputs to the display device according to the embodiment.

Subsequently, the output unit 406e outputs the placement period information to the display device 3 (step S113). Specifically, as illustrated in FIG. 13, the output unit 406e outputs placement period information M1 and an observation image P10 that is a display image to the display device 3. The placement period information M1 contains m1 of a maximum invasion degree (a maximum depth of invasion based on the fluorescence intensity), m2 on whether it is necessary to place a stent, and m3 of a preferred placement period for a stent.

Thereafter, the controller 409 determines whether a change signal that changes the observation mode to the normal light observation mode is input from the input unit 407 or the operation unit 22 of the endoscope 2 (step S114). When the controller 409 determines that the change signal that changes the observation mode to the normal light observation mode is input from the input unit 407 or the operation unit 22 of the endoscope 2 (YES at step S114), the endoscope system 1 moves to step S115 described below. On the other hand, when the controller 409 determines that the change signal that changes the observation mode to the normal light observation mode is not input from the input unit 407 or the operation unit 22 of the endoscope 2 (NO at step S114), the endoscope system 1 returns to step S104 described above.

At step S115, the controller 409 causes the first light source unit 402 to emit light by controlling the light source controller 404, thereby causing application of white light.

Subsequently, the image processor 406 acquires an imaging signal from the imaging device 204 of the endoscope 2, generates an observation image, and outputs the observation image to the display device 3 (step S116). Specifically, the generator 406a acquires an imaging signal from the imaging device 204 and, based on the imaging signal, generates an observation image.

Thereafter, the controller 409 determines whether there is invasion of living tissue by a laser according to the estimator 406d (step S117). Specifically, the controller 409 determines whether the estimator 406d estimates placement of a stent in the urinary tract and, when the estimator 406d estimates placement of a stent in the urinary tract, determines that there is invasion of living tissue by a laser. When the controller 409 determines that there is invasion of living tissue by a laser (YES at step S117), the endoscope system 1 moves to step S118 described below. On the other hand, when the controller 409 determines that there is no invasion of living tissue by a laser (NO at step S117), the endoscope system 1 moves to step S119 described below.

At step S118, the output unit 406e superimposes the placement period information indicating whether it is necessary to place a stent and the placement period onto the observation image that is generated by the generator 406a and outputs the observation image with the placement period information superimposed thereon to the display device 3. After step S118, the endoscope system 1 moves to step S120 described below.

At step S119, the output unit 406e outputs the observation image that is generated by the generator 406a to the display device 3. After step S119, the endoscope system 1 moves to step S120 described below.

At step S120, the controller 409 determines whether an end signal that ends observation of the subject is input from the input unit 407 or the operation unit 22 of the endoscope 2. When the controller 409 determines that the end signal that ends observation of the subject is input from the input unit 407 or the operation unit 22 of the endoscope 2 (YES at step S120), the endoscope system 1 ends the process. On the other hand, when the controller 409 determines that the end signal that ends observation of the subject is not input from the input unit 407 or the operation unit 22 of the endoscope 2 (NO at step S120), the endoscope system 1 returns to step S101 described above.

According to the embodiment described above, because the estimator 406d estimates a placement period during which the medical tool is placed in a lumen based on a fluorescence intensity that is calculated by the calculator 406c and the output unit 406e outputs placement period information on the placement period that is estimated by the estimator 406d and an observation image obtained by capturing an image of living tissue to the display device 3, it is possible to objectively know the placement period during which the medical tool is placed in a lumen.

According to the embodiment, because the estimator 406d estimates a degree of invasion of living tissue with an energy device based on a fluorescence intensity that is calculated by the calculator 406c and estimates a placement period based on the degree of invasion, it is possible to objectively know the placement period during which the medical tool is placed in a lumen.

According to the embodiment, because the estimator 406d estimates a degree of invasion based on correlation information that is recorded by the correlation information recorder 408b and a fluorescence intensity that is calculated by the calculator 406c, it is possible to estimate an actual degree of invasion of living tissue.

According to the embodiment, because the estimator 406d makes an estimation on whether to place the medical tool in a lumen based on a fluorescence intensity that is calculated by the calculator 406c, a user, such as a practitioner, is able to objectively know whether it is necessary to place the medical tool in the lumen.

According to the embodiment, when a plurality of fluorescence areas are extracted by the extractor 406b, because the estimator 406d estimates a placement period during which the medical tool is placed in a lumen based on the highest fluorescence intensity among those of the fluorescence areas, it is possible to support the most appropriate information in the situation of the sequential treatment.

In the embodiment, the output unit 406e outputs the observation image and the placement period information to the display device 3. For example, the observation image with the placement period information being superimposed thereon may be output to the display device 3.

Figure 14:
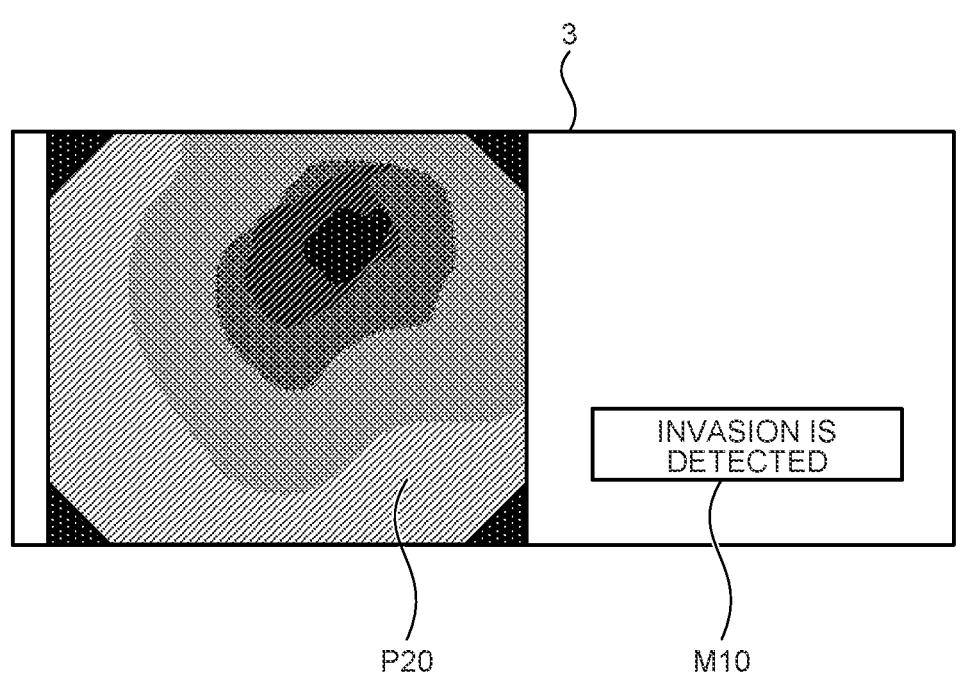
FIG. 14 is a diagram illustrating another example of the output screen that the output unit of the endoscope system outputs to the display device according to the embodiment.

In the embodiment, the output unit 406e outputs the placement period information to the display device 3; however, embodiments are not limited to this, and for example, when the estimator 406d estimates invasion of living tissue with the laser irradiation device 5, an output indicating that invasion of living tissue is detected may be made. Specifically, as illustrated in FIG. 14, when the estimator 406d estimates invasion of living tissue with the laser irradiation device 5, the output unit 406e may output invasion information M10 indicating that invasion of living tissue is detected to the display device 3. Accordingly, the practitioner is able to know invasion of living tissue with the laser irradiation device 5.

Figure 15:
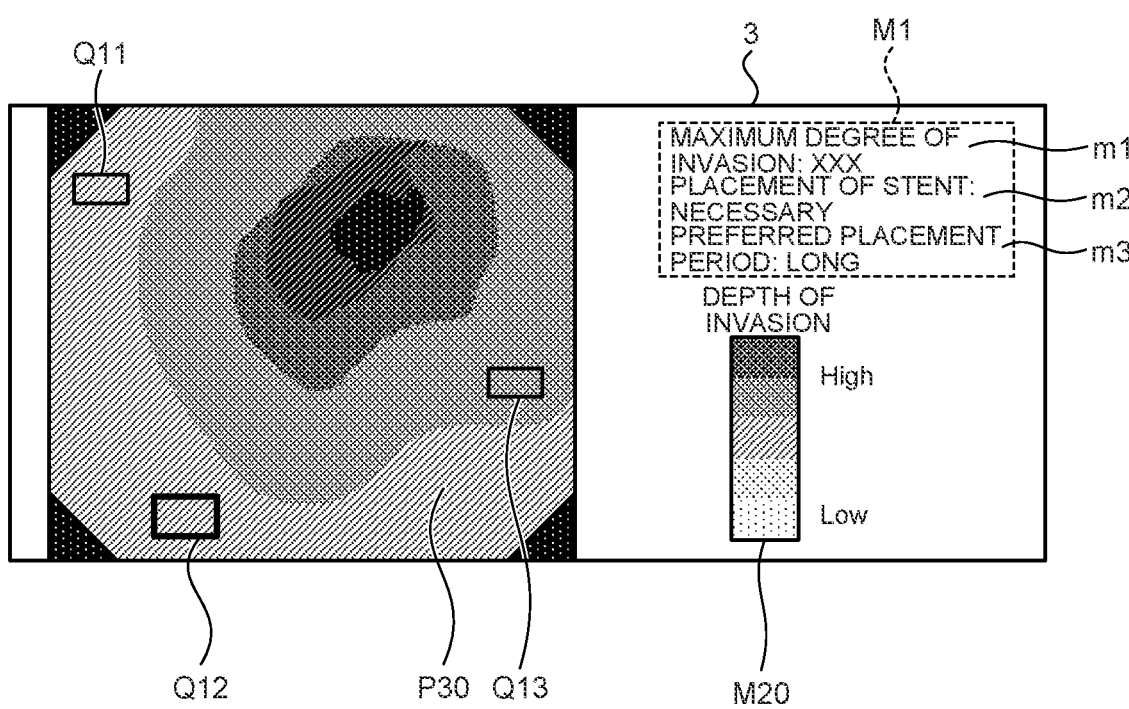
FIG. 15 is a diagram illustrating another example of the output screen that the output unit of the endoscope system outputs to the display device according to the embodiment.
Figure 16:
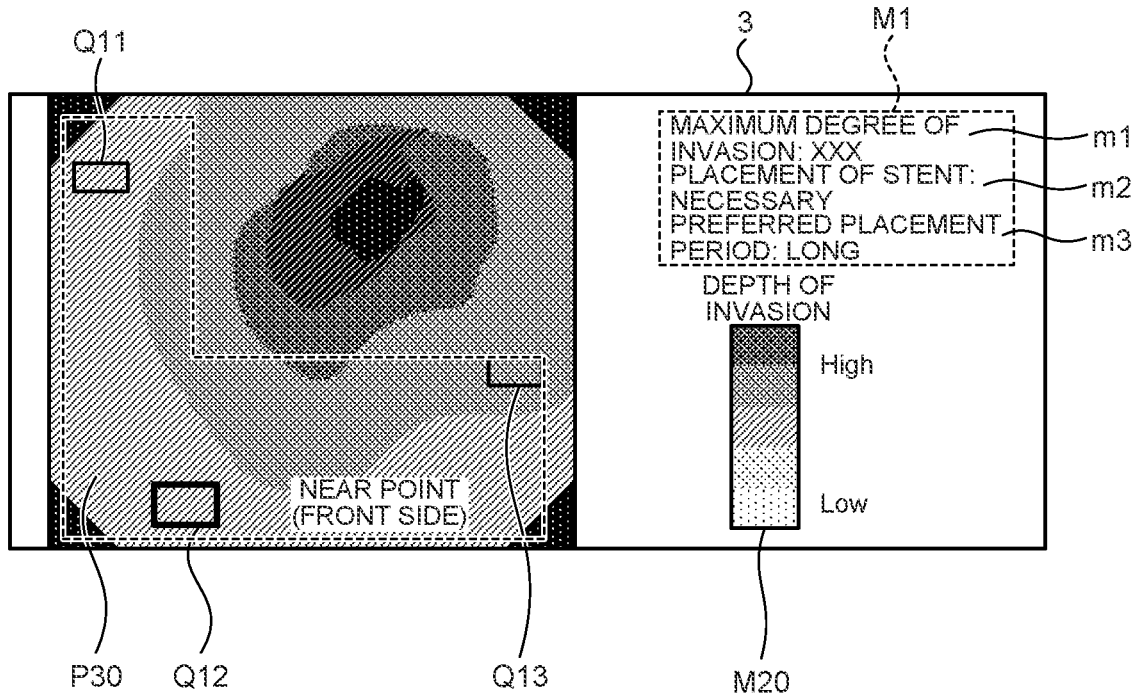
FIG. 16 is a diagram illustrating another example of the output screen that the output unit of the endoscope system outputs to the display device according to the embodiment.

In the embodiment, the output unit 406e outputs the placement period information to the display device 3; however, embodiments are not limited thereto and, for example, when the calculator 406c calculates each of light emission intensities of the fluorescence areas, an output to the display device 3 may be made such that degrees of invasion of the respective fluorescence areas are identifiable. Specifically, as illustrated in FIG. 15, the output unit 406e may superimposes the degrees of invasion on an observation image P30 in a display mode corresponding to the light emission intensities of the fluorescence areas Q11 to Q13 that are calculated by the calculator 406c and depth information M20 on invasion depths and the placement period information M1 may be output together to the display device 3. In this case, the estimator 406d estimates whether it is necessary to place a stent and a placement period based on the light emission intensity of a fluorescence area Q12 on a near-point side compared to that of the light emission intensities of fluorescence areas Q11 and Q13 on a far-point side among the fluorescence areas Q11 to Q13 in an area H1 illustrated in FIG. 16. As for a method of determining the far-point side and the near-point side, the estimator 406d determines whether luminance information on each pixel of the observation image (white light image) is at or above a given threshold, estimates that pixels at or above the given threshold are on the near-point side and estimates that pixels under the given threshold are on the far-point side, thereby estimating the far-point side and the near-point side. When the extractor 406b detects a fluorescence area on only the far-point side, the output unit 406e may make only an output indicating that invasion of living tissue with the energy device is caused to the display device 3. Furthermore, when the extractor 406b detects a fluorescence area on only the far-point side, the calculator 406c may calculate a fluorescence intensity by performing amplification using a gain, etc., on the signal values of pixels positioned in the fluorescence area.

In the embodiment, the practitioner switches the observation mode by operating the input unit 407 or the operation unit 22, thereby switching between the observation image and the fluorescence image. Alternatively, a fluorescence image may be acquired by applying excitation light by automatic switching at a given frame rate (for example, 60 fps) and at every given frames (for example, 10 fps). In this case, while outputting the observation image to the display device 3, the output unit 406e may output invasion information M10 indicating that invasion of living tissue is detected only when the estimator 406d estimates a degree of invasion with the energy device.

In the embodiment, the estimator 406d estimates whether it is necessary to place a stent and estimates a placement period during which a stent is placed in the urinary tract; however, embodiments are not limited thereto and, for example, the estimator 406d may make only any one of an estimation on whether it is necessary to place a stent and an estimation of a placement period during which a stent is placed in the urinary tract. Needless to say, the estimator 406d may make only any one of an estimation on whether it is necessary to place a stent and an estimation of a placement period during which a stent is placed in the urinary tract according to an operation on the input unit 407 or the operation unit 22 by the practitioner.

Modification 1

Figure 17:
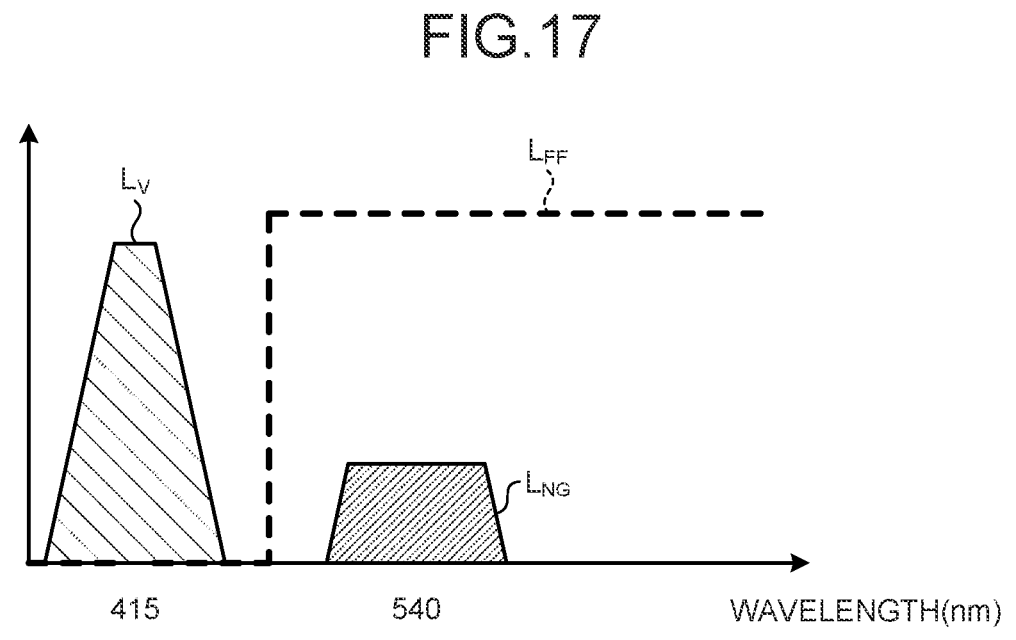

In the embodiment, the transmission characteristics of the cut filter 203 are changeable. FIG. 17 is a diagram schematically illustrating transmission characteristics of a cut filter according to a modification of the embodiment. In FIG. 17, the horizontal axis represents the wavelength (nm) and the vertical axis represents the transmission characteristics. In FIG. 17, the polygonal chain $L_{FF}$ represents transmission characteristics of a cut filter 203A, the polygonal chain $L_V$ represents the wavelength characteristics of the excitation light, and the polygonal chain $L_{NG}$ represents the wavelength characteristics of fluorescence caused by application of the excitation light to advanced glycation end products caused by thermal treatment on living tissue performed by an energy device, for example, the laser application device 5.

As represented by the polygonal chain $L_V$ and the polygonal chain $L_{NG}$, the cut filter 203A transmits part of the excitation light that is reflected from the living tissue of the observation area and transmits only fluorescence components. Specifically, the cut filter 203A blocks light having a wavelength band on a short-wavelength side from 400 nm and under 430 nm containing the excitation light and transmits light having a wavelength band on a long wavelength side from 430 nm containing fluorescence caused by application of excitation light to advanced glycation end products caused by thermal treatment.

Other Embodiments

It is possible to form various embodiments by appropriately combining a plurality of elements disclosed in the endoscope system according to the embodiment described above. For example, some elements may be omitted from the entire elements described with respect to the endoscope system according to the embodiment described above. Furthermore, the elements described with respect to the endoscope system according to the embodiment described above may be combined as appropriate.

In the embodiment, the first light source unit, the second light source unit and the light source controller are provided integrally; however, embodiments are not limited thereto. For example, a light source device including the first light source unit, the second light source unit and the light source controller and a control device may be provided independently.

In the embodiment, the endoscope system uses a flexible endoscope; however, embodiments are not limited thereto, and an endoscope system using a rigid endoscope, a medical surgery robot using a plurality of rigid endoscopes and a laser irradiation device, or a medical observation system is also usable.

In the endoscope system according to the embodiment, the "unit", "-er" and "-or" described above may be read as "means", "circuitry", or the like. For example, the controller may be read as a control means or a control circuitry.

In the description of the flowcharts herein, the context of the process among steps is clearly specified using expressions including "first of all", "thereafter", and "subsequently"; however, the order of the processes necessary to implement the disclosure is not uniquely determined by those expressions. In other words, the order of processes in the flowcharts described herein is changeable within a range without inconsistency.

Some embodiments of the present application have been described above in detail according to the drawings and the embodiments are exemplary and, starting from the modes described in the disclosure section, the disclosure can be carried out in other modes on which various modifications and improvements are made according to the knowledge of those skilled in the art.

The disclosure can also employ the following manipulation:

(1) A manipulation method of flexible transurethral lithotomy using an endoscope system, the manipulation method comprising:

inserting an endoscope into a urinary tract of a subject by white light observation;

fragmenting a calculus that is positioned in the urinary tract by applying a laser to the calculus;

extracting the calculus that is fragmented by the laser from the urinary tract;

switching an observation method performed by the endoscope to fluorescence observation;

internally observing the subject by fluorescence observation; and placing a stent after observation by the fluorescence observation.

According to the disclosure, an effect that it is possible to objectively know a placement period during which a medical tool is placed in a lumen is achieved.

What is claimed is:

1. An assist device comprising:

a processor configured to:

generate a fluorescence image based on an imaging signal generated by capturing an image of fluorescence caused by an excitation light applied to a living tissue;

calculate a fluorescence intensity based on the fluorescence image;

based on the calculated fluorescence intensity and correlation information representing a previously measured correlation between a degree of invasion of the living tissue by an energy device and a fluorescence intensity, estimate a placement period during which a medical tool is placed in a lumen of the living tissue; and cause placement period information to be displayed together with an observation image of the living tissue to assist placement of the medical tool.

2. The assist device according to claim 1, wherein the processor is configured to make an estimation on whether to place the medical tool in the lumen.

3. The assist device according to claim 1, wherein the processor is configured to superimpose the placement period information onto the observation image and output the observation image with the placement period information superimposed thereon.

4. The assist device according to claim 1, wherein the processor is configured to extract a fluorescence area of a plurality of fluorescence areas from the fluorescence image and, when the plurality of fluorescence areas are extracted, estimate the placement period based on a highest fluorescence intensity.

5. The assist device according to claim 4, wherein the imaging signal is obtained by capturing an image of a urinary tract that extends in a depth direction, and the processor is configured to, when the plurality of fluorescence areas are extracted, estimate the placement period based on a fluorescence intensity of a fluorescence area of the plurality of fluorescence areas that is positioned on a side of a near point that is the closest to an imaging optical system.

6. The assist device according to claim 5, wherein the lumen includes the urinary tract.

7. The assist device according to claim 4, wherein the processor is configured to, when the plurality of fluorescence areas are extracted, output the plurality of fluorescence areas such that each of the plurality of fluorescence areas is identifiable based on a fluorescence intensity of each of the plurality of fluorescence areas.

8. The assist device according to claim 1, wherein the excitation light causing the fluorescence image has a wavelength band from 390 nm to 430 nm, the fluorescence used to estimate the placement period has a wavelength band from 500 nm to 640 nm, and the imaging signal is obtained by capturing an image of transmission light that passes through a cut filter that blocks excitation wavelengths shorter than 430 nm.

9. The assist device according to claim 1, further comprising:

a memory configured to store the correlation information, wherein the processor is configured to:

based on the calculated fluorescence intensity and the correlation information stored in the memory, determine whether placement of the medical tool in the lumen of the living tissue is necessary.

10. An endoscope system comprising:

an endoscope that is insertable into a lumen of a subject;

a light source configured to emit excitation light that excites advanced glycation end products caused by performing thermal treatment on a living tissue; and a control device that is detachable from the endoscope, the endoscope including an imaging device configured to generate an imaging signal by capturing an image of fluorescence caused by the excitation light, and a cut filter that is provided on a side of a light receiving surface of the imaging device, the cut filter being configured to block light on a side of short wavelengths containing part of a wavelength band of the excitation light, the control device including an assist device that assists a practitioner, and the assist device including a processor configured to:

generate a fluorescence image based on the imaging signal, calculate a fluorescence intensity based on the fluorescence image, based on the calculated fluorescence intensity and correlation information representing a previously measured correlation between a degree of invasion of the living tissue by an energy device and a fluorescence intensity, estimate a placement period during which a medical tool is placed in the lumen of the living tissue, and cause placement period information to be displayed together with an observation image of the living tissue to assist placement of the medical tool.

11. An assist method executed by an assist device, the method comprising:

generating a fluorescence image based on an imaging signal that is generated by capturing an image of fluorescence caused by excitation light that is applied to a living tissue;

calculating a fluorescence intensity based on the fluorescence image;

based on the calculated fluorescence intensity and correlation information representing a previously measured correlation between a degree of invasion of the living tissue by an energy device and a fluorescence intensity, estimating a placement period during which a medical tool is placed in a lumen; and causing placement period information to be displayed together with an observation image of the living tissue to assist placement of the medical tool.

12. A non-transitory computer-readable recording medium with an executable program stored thereon, the program causing an assist device to execute generating a fluorescence image based on an imaging signal that is generated by capturing an image of fluorescence caused by excitation light that is applied to a living tissue;

calculating a fluorescence intensity based on the fluorescence image;

based on the calculated fluorescence intensity and correlation information representing a previously measured correlation between a degree of invasion of the living tissue by an energy device and a fluorescence intensity, estimating a placement period during which a medical tool is placed in a lumen of the living tissue; and causing placement period information to be displayed together with an observation image of the living tissue to assist placement of the medical tool.

13. An assist device comprising:

a processor configured to:

generate a fluorescence image based on an imaging signal generated by capturing an image of fluorescence caused by an excitation light applied to a living tissue;

calculate a fluorescence intensity based on the fluorescence image;

based on the calculated fluorescence intensity and correlation information representing a previously measured correlation between a degree of invasion of the living tissue by an energy device and a fluorescence intensity, estimate a presence or absence of a medical tool in the living tissue; and cause information indicating the presence or absence of the medical tool to be displayed together with an observation image of the living tissue to assist placement of the medical tool.

\* \* \* \* \*